United States Patent
Henner et al.

(10) Patent No.: US 6,521,608 B1
(45) Date of Patent: Feb. 18, 2003

(54) VITAMIN D AND ITS ANALOGS IN THE TREATMENT OF TUMORS AND OTHER HYPERPROLIFERATIVE DISORDERS

(75) Inventors: William D. Henner, Portland, OR (US); Tomasz M. Beer, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 09/647,075

(22) PCT Filed: Mar. 25, 1999

(86) PCT No.: PCT/US99/06442

§ 371 (c)(1),
(2), (4) Date: Sep. 21, 2000

(87) PCT Pub. No.: WO99/49870

PCT Pub. Date: Oct. 7, 1999

Related U.S. Application Data

(60) Provisional application No. 60/079,696, filed on Mar. 27, 1998.

(51) Int. Cl.⁷ ............................................. A61K 31/59
(52) U.S. Cl. ........................................ 514/167; 514/168
(58) Field of Search ................................. 514/167, 168

(56) References Cited

U.S. PATENT DOCUMENTS

| | | |
|---|---|---|
| 4,391,802 A | 7/1983 | Suda et al. |
| 4,717,721 A | 1/1988 | DeLuca et al. |
| 4,804,502 A | 2/1989 | Baggiolini et al. |
| 4,851,401 A | 7/1989 | DeLuca et al. |
| 4,857,518 A | 8/1989 | DeLuca et al. |
| 4,866,048 A | 9/1989 | Calverley et al. |
| 4,897,387 A | 1/1990 | Ikekawa et al. |
| 4,927,815 A | 5/1990 | DeLuca et al. |
| 5,120,722 A | 6/1992 | Baggiolini et al. |
| 5,145,846 A | 9/1992 | Baggiolini et al. |
| 5,190,935 A | 3/1993 | Binderup et al. ........... 514/167 |
| 5,237,110 A | 8/1993 | DeLuca et al. |
| 5,292,728 A | 3/1994 | Neef et al. ................ 514/167 |
| 5,354,744 A | 10/1994 | DeLuca et al. |
| 5,374,629 A | 12/1994 | Calverley et al. |
| 5,403,940 A | 4/1995 | Valles et al. |
| 5,411,949 A | 5/1995 | Neef et al. |
| 5,446,034 A | 8/1995 | Bretting et al. |
| 5,446,035 A | 8/1995 | Neef et al. |
| 5,447,924 A | 9/1995 | Bretting |
| 5,547,947 A | 8/1996 | Dore et al. |
| 5,763,429 A | 6/1998 | Bishop et al. .............. 514/168 |
| 5,786,348 A | 7/1998 | Bishop et al. .............. 514/167 |
| 5,795,882 A | 8/1998 | Bishop et al. .............. 514/170 |
| 5,798,345 A | 8/1998 | Knutson et al. ............ 514/167 |
| 5,939,456 A | 8/1999 | Perrine ..................... 514/554 |
| 6,028,064 A | 2/2000 | Rodriguez et al. |
| 6,034,074 A | 3/2000 | Rodriguez et al. |
| 6,087,350 A | 7/2000 | Johnson et al. ............ 514/168 |

FOREIGN PATENT DOCUMENTS

| | | |
|---|---|---|
| JP | 62 185015 | 8/1987 |
| WO | WO 96/00074 | 1/1996 |
| WO | WO 96/03994 | 2/1996 |
| WO | WO 97/41096 | 11/1997 |
| WO | WO00/61112 | 10/2000 |
| WO | WO01/64251 A2 | 3/2001 |

OTHER PUBLICATIONS

Campbell MJ, Koeffler HP: Toward therapeutic intervention of cancer by vitamin D compounds. Journal of the National Cancer Institute, 89:182, 1997.

Cohen SM, Saulenas AM, Sullivan CR, et al: Further studies of the effect of vitamin D on retinoblastoma. Archives of Opthalmology, 106:541, 1988.

Colston KW, Berger U, Coombes RC: Possible role for vitamin D in controlling breast cancer cell proliferation. Lancet, 1:188, 1989.

Colston KW, Chander SK, Mackay AG, et al: Effects of synthetic vitamin D analogues on breast cancer cell proliferation in vivo and in vitro. Biochemical Pharmacology, 44:693, 1992.

Colston K, Colston MJ, Feldman D: 1,25–Dihydroxyvitamin D3 and malignant melanoma: the presence of receptors and inhibition of cell growth in culture. Endocrinology, 108:1083, 1981.

Cross HS, Huber C, Peterlik M: Antiproliferative effect of 1,25–dihydroxyvitamin D3 and its analogs on human colon adenocarcinoma cells (Caco–2). Influence of extracellular calcium. Biochemical and Biophysical Research Communications, 179:57, 1991.

Cross HS, Farsoudi KH, Peterlik M: Growth inhibition of human colon adenocarcinoma–derived Caco–2 cells by 1,25–dihydroxyvitamin D3 and two synthetic analogs: relation to in vitro hypercalcemic potential. Archives of Pharmacology, 347:105, 1993.

Drivdahl RH, Loop SM, Andress DL, et al: IGF–binding proteins in human prostate tumor cells: expression and regulation by 1,25–dihydroxyvitamin D3. Prostate, 26:72, 1995.

Eisman JA, Barkla DH, Tutton PJM: Suppression of in vivo growth of human solid tumor xenografts by 1,25–dihydroxyvitamin D3. Cancer Research, 47:21, 1987.

(List continued on next page.)

Primary Examiner—Theodore J. Criares
Assistant Examiner—Jennifer Kim
(74) Attorney, Agent, or Firm—Klarquist Sparkman, LLP

(57) ABSTRACT

Treatment of hyperporliferative disorders (including tumors and psoriasis) by pulse administration of a drug (such as Vitamin D or an analog) that increases blood or tissue levels of Vitamin D. The drug is administered at a sufficient dose to have an anti-proliferative effect, but the pulsed administration of the drug avoids the development of severe symptomatic or life-threatening hypercalcemia. In particular embodiments, avoidance of hypercalcemia (as measured by serum levels of calcium above normal range) is avoided altogether. In a particular example, the drug is calcitriol administered at an oral dose of about 0.5 mcg/kg once a week.

54 Claims, 1 Drawing Sheet

OTHER PUBLICATIONS

Geusens P, Vanderschueren D, Verstraeten A, et al: Short-term course of 1,25(OH)2D3 stimulates osteoblasts but not osteoclasts in osteoporosis and osteorthrits. Clacified Tissue International, 49:168, 1991.

Hansen, C. Mork et al., "Seocalcitol (EB 1089): A Vitamin D Analogue of Anti–cancer Potential. Background, Design, Synthesis, Pre–clinical and Clinical Evaluation," *Current Pharmaceutical Design*, 2000, 6, 803–828.

Haugen JD, Pittelkow MR, Zinsmeister AR, et al: 1alpha, 25–dihydroxyvitamin D3 inhibits normal human keratinocyte growth by increasing transforming growth factor $_{62}$2 release. Biochemical and Biophysical Research Communications., 229:618, 1996.

Hedlund TE, Moffatt KA, Miller GJ: Stable expression of the nuclear vitamin D receptor in the human prostatic carcinoma cell line JCA–1: evidence that the antiproliferative effects of $1_\alpha$, 25–dihydroxyvitamin D3 are mediated exclusively through the genomic signaling pathway. Endocrinology, 137:1554, 1996.

Hedlund TE, Moffatt KA, Miller GJ: Vitamin D receptor expression is required for growth modulation by $1_\alpha$,25–dihydroxyvitamin D3 in human prostatic carcinoma cell line ALVA–31. Journal of Steroid Biochemistry and Molecular Biology, 58:277, 1996.

Hengst L, Reed SI: Translational control of p27 Kip1 accumulation during the cell cycle. Science, 271:1861, 1996.

Higashimoto Y, Ohata M, Nishio K, et al: 1 alpha, 25–dihydroxyvitamin D3 and all–trans–retinoic acid inhibit the growth of a lung cancer cell line. Anticancer Res, 16:2653, 1996.

Holick MF: Noncalcemic actions of 1,25–dihydroxyvitamin D3 and clinical applications. Bone, 17:107S, 1995.

Honma Y, Hozumi M, Abe E, et al: $1_{60}$,25–dihydroxyvitamin D3 and $1_\alpha$–hydroxyvitamin D3 prolong survival time of mice inoculated with myeloid leukemia cells. Proceedings of the National Academy of Sciences USA, 80:201, 1983.

Huang et al., Glucocoritcoid and Developmental Expression of the RAT 1,25 Dihydroxyvitamin D3 Receptor Gene: Comparison to Calbindin Gene Expression, *Journal of Bone and Mineral Research*, Programs & Abstracts, #441, Sep. 10, 1989, Aug. 1989, vol. 4.

James SY, Mackay AG, Colston KW: Effects of 1,25 dihydroxyvitamin D3 and its analogues on induction of apoptosis in breast cancer cells. Journal of Steroid Biochem Molec Biol, 58:395, 1996.

Kim HJ, Abdelkader N, Katz M, et al: 1,25–dihydroxy–vitamin–D3 enhances antiproliferative effect and transcription of TGF–beta1 on human keratinocytes in culture. Journal of Cellular Physiology, 151:579, 1992.

Kobayashi T, Hashimoto K, Yoshikawa K: Growth inhibition of human keratinocytes by 1,25–dihydroxyvitamin D3 is linked to dephosphorylation of retinoblastoma gene product. Biochem Biophys Research Communications, 196:487, 1993.

Koeffler HP, Hirji K, Itri L: 1,25–Dihydroxyvitamin D3: in vivo and in vitro effects on human preleukemic and leukemic cells. Cancer Treatment Reports, 69:1399, 1985.

Koli K, Keski–Oja J: 1,25–dihydroxyvitamin D3 enhances the expression of transforming growth factor $_\beta$1 and its latent form binding protein in cultured breast carcinoma cells. Cancer Research, 55:1540, 1995.

Lapco PE, Light BW, Konety BR, et al: In vitro effects of 1,25–dihydroxycholecalciferol on Dunning Prostate Cancer Cells. Proceedings of the American Association of Cancer Research, 38:456, 1997.

Liu, M, Lee MH, Cohen M, et al: Transcriptional activation of the Cdk inhibitor p21 by vitamin D3 leads to the induced differentiation of the myelomonocytic cell line U937. Genes Dev, 10:142, 1996.

McElwain MC, Dettelbach MA, Modzelewski RA, et al: Antiproliferative effects in vitro and in vivo of 1,25–dihydroxyvitamin D3 analog in a squamous cell carcinoma model system. Mol Cel Diff, 3:31, 1995.

Mason RS, Lissner D, Posen S, et al: Blood concentrations of dihydroxylated vitamin D metabolites after an oral dose. British Medical Journal, :449, 1980.

Majewski S, Szmurlo A, Marczak M, et al: Inhibition of tumor cell–induced angiogenesis by retinoids, 1,25–dihydroxyvitamin D3 and their combinations. Cancer Letters, 75:35, 1993.

Majewski S, Marczak M, Szmurlo A, et al: Retinoids, interferon alpha, 1,25–dihydroxyvitamin D3 and their combinations inhibit angiogenesis induced by non–HPV–harboring tumor cell lines. $RAR_\alpha$ mediates the antiangiogenic effect of retinoids. Cancer Letters, 89:117, 1995.

Mazess, R.B & Barden, H.S., Is Age a Factor in Osteoporotic Fractures?, *Journal of Bone and Mineral Research*, Programs & Abstracts, #442, Sep. 10, 1989, Aug. 1989, vol. 4.

Mehta RG, Moriarty RM, Mehta RR, et al: Prevention of paraneoplastic mammary lesion development by a novel vitamin D analogue, $1_\alpha$–hydroxyvitamin D5. Journal of the National Cancer Institute, 89:212, 1997.

Mercier T, Chaumontet C, Gaillard–Sanchez I, et al: Calcitriol and Lexicalcitriol (KH1060) inhibit the growth of human breast adenocarcinoma cells by enhancing transforming growth factor–beta production. Biochemical Pharmacology, 52:505, 1996.

Munker R, Kobayashi T, Elstner E, et al: A new series of vitamin D analogs in highly active for clonal inhibition, differentiation, and induction of WAF1 in myeloid leukemia. Blood, 88:2201, 1996.

Oikawa T, Hirotani K, Ogasawara H, et al: Inhibition of angiogenesis by vitamin D3 analogues. European Journal of Pharmacology, 178:247, 1990.

Ostrem, Voula K. et al., "24–and 26–homo 1,25–dihydroxyvitamin $D_3$: Preferential activity in inducing differentiation of human leukemia cells HL–60 in vitro," *Proc. Natl. Acad. Sci. USA*, vol. 84, pp 2610–2614, May 1987, Biochemistry.

Papapoulos SE, Clemens TL, Sandler LM, et al: The effect of renal function on changes in circulating concentration of 1,25–dihydroxycholecalciferol after an oral dose. Clinical Science, 62:427, 1982.

Rozen F, Yang XF, Huynh H, et al: Antiproliferative action of 1,25–dihydroxyvitamin D3 and its analogues on MCF–7 breast cancer cells is related to increased insulin–like growth factor binding protein–5 accumulation. Proceedings of the American Association of Cancer Research, 38:456, 1997.

Rustin GJ, Quinell TG, Johnson J, et al: Trial of isotretinoin and calcitriol monitored by CA 125 in patients with ovarian cancer. British Journal of Cancer, 74:1479, 1996.

Scharla SH, Strong DD, Subburaman M, et al: 1,25–dihydroxyvitamin D3 differentially regulates the production of insulin–like growth factor I (IGF–I) and IGF–binding protein–4 in mouse osteoblasts. Endocrinology, 129:3139, 1991.

Schwartz GG, Wang MH, Zhang M, et al: 1alpha, 25–dihydroxyvitamin D (calcitriol) inhibits the invasiveness of human prostate cancer cells. Cancer Epidemiology, Biomarkers & Prevention, 6:727, 1997.

Schwartz GG, Oeler TA, Uskokovic MR, et al: Human prostate cancer cells: inhibition of proliferation by vitamin D analogs. Anticancer Research, 14:1077, 1994.

Shababang M, Buffan AE, Nolla JM, et al: The effect of 1,25–dihydroxyvitamin D3 on the growth of soft–tissue sarcoma cells as mediated by the vitamin D receptor. Annals of Surgical Oncology, 3:144, 1996.

Shokravi MT, Marcus DM, Alroy J, et al: Vitamin D inhibits angiogenesis in transgenic murine retinoblastoma. Investigative Opthalmology & Visual Science, 36:83, 1995.

Simboli–Cambell M, Narvaez CJ, van Weelden K, et al: Comparative effects of 1,25(OH)2D3 and EB1089 on cell cycle kinetics and apoptosis in MCF–7 breast cancer cells. Breast Cancer Research and Treatment, 42:31, 1997.

Skowronski JS, Peehl DM, Feldman D: Vitamin D and prostate cancer: 1,25–dihydroxyvitamin D3 receptors and actions in human prostate cancer cell lines. Endocrinology, 132:1952, 1993.

Skowronski JS, Peehl DM, Feldman D: Actions of vitamin D3 analogues on human prostate cancer cell lines: comparison with 1,25–dihydroxyvitamin D3. Endocrinology, 136:20, 1995.

Stern et al., Homo Analogs of 1.25–Dihydroxyvitamin D3 allow Dissociation of in vitro bone resorption and in vivo calcium mobilization from HL–60 Cell Differentiation, *Journal of Bone and Mineral Research*, Programs & Abstracts, #440, Sep. 10, 1989, Aug. 1989, vol. 4

Tang W, Ziboh VA, Isseroff RR, et al: Novel regulatory action of 1alpha, 25–dihydroxyvitamin D3 on the metabolism of polyphosphoinositides in murine epidermal keratinocytes. Journal of Cell Physiology, 132:131, 1987.

Veenstra TD, Windebank AJ, Kumar R: 1,25–dihydroxyvitamin D3 regulates the expression of N–myc, c–myc, protein kinase C, and transforming growth factor–beta2 in neuroblastoma cells. Biochemical and Biophysical Research Communications, 235:15, 1997.

Velez–Yanguas MC, Kalebic T, Maggi M, et al: $1_\alpha$,25–dihydroxy–16–Ene–23–yne–26,27hexaflurocholecalciferol (Ro24–5531) modulation of insulin–like growth factor–binding protein–3 and induction of differentiation and growth arrest in a human osteosarcoma cell line. Journal of Clinical Endocrinology and Metabolism, 81:93, 1996.

Vink–van Wijngaarden T, Pols HA, Buurman CJ, et al: Inhibition of insulin– and insulin–like growth factor–1–stimulated growth of human breast cancer cells by 1,25–dihydroxyvitamin D3 and vitamin D3 analogue EN1089. European Journal of Cancer, 32A:848, 1996.

Wang QM, Jones JB, Studzinski GP: Cyclin–dependent kinase inhibitor p27 as a mediator of the G1–S phase block induced by 1,25–dihydroxyvitamin D3 and HL60 cells. Cancer Research, 56:264, 1996.

Yabushita H, Hirata M, Noguchi M, et al: Vitamin D receptor in endometrial carcinoma and the differentiation-inducing effect of 1,25–dihydroxyvitamin D3 on endometrial carcinoma cell lines. Journal of Obstetrics and Gynaecology Research, 22:529, 1996.

Yamazaki, et al., Bone Mineral Density of the Spine (L2–L4) and Femoral Neck in Normal Japanese Subjects Using X–Ray Absorptiometry, *Journal of Bone and Mineral Research*, Programs & Abstracts, #443, Sep. 10, 1989, Aug. 1989, vol. 4.

Zhou JY, Norman AW, Lubbert M: Novel vitamin D analogs that modulate leukemic cell growth and differentiation with little effect on intestinal calcium absorption or bone calcium mobilization. Blood, 74:82, 1989.

Zhuang SH, Schwartz GG, Cameron D, et al: Vitamin D receptor content and transcriptional activity do not fully predict antiproliferative effects of vitamin D in human prostate cancer cell lines. Molecular and Cellular Endocrinology, 126:83, 1997.

Zugmaier G, Jager R, Grage B, et al: Growth–inhibitory effects of vitamin D analogues and retinoids on human pancreatic cancer cells. British Journal of Cancer, 73:1341, 1996.

Bouillon et al., *Endocrine Reviews*, 16:2, 200–257 1995.

Buras et al., *Breast Cancer Res. Treat.*, 31:191–202, 1994.

Miller et al., *Clin. Cancer Res.*, 1:997–1003, Sep. 1995.

Osborn et al., *Urol. Oncol.*, 1:195–198, 1995.

Peehl et al., *Cancer Research*, 54:805–810, 1994.

Welsh, *Biochem. Cell Biol.*, 72:537–545, Dec. 8, 1994.

*Dietary Vitamin Supplements*, Therapuetic Products Directorate (monograph), May 28, 1997.

Smith et al., *A Phase I Trial of Calcitriol (1,25–Dihydroxycholecalciferol) in Patients with Advanced Malignancy*, Clinical Cancer Research, vol. 5, 1339–1345, Jun. 1999.

Gross et al., *Treatment of Early Recurrent Prostate Cancer with 1,25–Dihydroxyvitamin D3 (Calcitriol)*, The Journal of Urology, vol. 159, 2035–2040, Jun. 1998.

Tsukamoto et al., *The Oral 1,25–Dihydroxyvitamin $D_3$ Pulse Therapy' in Hemodialysis Patients with Severe Secondary Hyperparathyroidism*, Nephron, 57:23–28, 1991.

Kyle et al., *Effect of Sodium Fluoride, Calcium Carbonate, and Vitamin D on the Skeleton in Multiple Myeloma*, Cancer 45:1669–1674, 1980.

Peng et al., *A Crossover Comparison of Intermittent Oral and Intravenous Administration of Calcitriol on the Parathyroid Hormone Concentration in Hemodialysis Patients*, Mineral and Electrolyte Metabolism, 23:13–18, 1997.

*Actions of Vitamin D3 Analogs on Human Prostate Cancer Cell Lines: Comparison with 1,25–Dihydroxyvitamin D3*, Endoctrinology (USA) 1995, 136/1 (20–26). (Abstract).

Knutson et al., *Pharmacokinetics and Systemic Effect on Calcium Homeostatis of 1 Alpha,24–Dihydroxyvitamin D2 in Rats. Comparison with 1alpha,25–Dihydroxyvitamin D2, Clacitriol, and Clacipotriol*, Biochem. Pharmacol., 53(6):829–37, 1997. (Abstract).

Gross et al., *Treatment of Early Recurrent Prostate Cancer with 1,25–Dihydroxyvitamin D3 (Calcitriol)*, Journal of Urology, 159(6):2035–39, 1998. (Abstract).

Berkow, et al., *The Merck Manual of Diagnosis* ($16^{th}$ ed.)(Merck Research Laboratories, Rahway, NJ 1992), p. 965.

Colston, et al., *The Lancet* vol. 1, iss. 8631, p. 188–92 (Jan. 28, 1989).

Eisman, et al., *Cancer Research* 47:21–25 (1987).

Ogata, E., *Calcified Tissue International* 60(1):130–33 (1997).

Srivastav, et al., *Can. J. Zool.* 65(8):2111–2112 (1987).

Osborn JL, Schwartz GG, Smith DC, et al: Phase II trial of oral 1,25–dihydroxyvitamin D (Calcitriol) in hormone refractory prostate cancer. Urologic Oncology, 1:195, 1995.

Tokuumi Y: Correlation between the concentration of 1,25 alpha dihydroxyvitamin D3 receptors and growth inhibition, and differentiation of human osteosarcoma cells induced by vitamin D3. Journal of the Japanese Orthopaedic Association, 69:181, 1995.

Abe E, Miyaura C, Sakagami H: Differentiation of rat myc leukemia cells induced by 1,25–dihydroxyvitamin D3. Proceedings of the National Academy of Sciences USA, 78:4990, 1981.

Albert DM, Saulenas AM, Cohen SM: Verhoeff's query: is vitamin D effective against retinoblastoma? Archives of Opthalmology, 106:536, 1988.

Bechtel, Ulrike et al., "Limitations of Pulse Oral Calcitriol Therapy in Continuous Ambulatory Peritoneal Dialysis Patients," *American Journal of Kidney Disease*, vol. 25, No. 2 (Feb.), 1995, pp. 291–296.

VITAMIN D AND ITS ANALOGS IN THE TREATMENT OF TUMORS AND OTHER HYPERPROLIFERATIVE DISORDERS

PRIORITY CLAIM

This is a §371 U.S. national stage of PCT/US99/06442, filed Mar. 25, 1999, which was published in English under PCT Article 21(2), and claims the benefit of U.S. application Ser. No. 60/079,696, filed Mar. 27, 1998.

FIELD OF THE INVENTION

This invention concerns the use of Vitamin D and its analogs in the treatment of tumors and hyperproliferative disorders.

BACKGROUND OF THE INVENTION

Vitamin D is a generic term for a family of secosteroids that have affinity for the Vitamin D receptor, and are involved in the physiologic regulation of calcium and phosphate metabolism. Exposure to the sun and dietary intake are common sources of Vitamin D, but deficiencies of this vitamin can cause rickets and osteomalacia. Supplementation of dairy and other food products has reduced the incidence of Vitamin D deficiency conditions in modern society, and medical research concerning this vitamin has turned to its therapeutic effects in a variety of pathological conditions.

Vitamin $D_3$ is synthesized in human skin from 7-dehydrocholesterol and ultraviolet light. Vitamin $D_3$, or its analog Vitamin $D_2$, can be ingested from the diet, for example in fortified milk products. Vitamin $D_2$ and $D_3$ undergo hydroxylation first in the liver to 25-hydroxyvitamin D, then in the kidney to $1\alpha,25$-dihydroxycholecalciferol (also known as 1,25-dihydroxyvitamin D or calcitriol), which is the principal biologically active form of Vitamin D. The biological production of this active form of the vitamin is tightly physiologically regulated.

Vitamin D exerts its calcium regulating activity through both genomic and nongenomic pathways. Although the nongenomic pathways remain poorly characterized, the genomic responses are mediated through binding to the nuclear Vitamin D receptor (VDR). The VDR is a ligand-activated transcription factor, which binds the Vitamin $D_3$ response element contained within the promoter/enhancer region of target genes. Vitamin D maintains calcium levels in the normal range by stimulating intestinal calcium absorption. When intestinal absorption is unable to maintain calcium homeostasis, Vitamin D stimulates monocytic cells to become mature osteoclasts, which in turn mobilize calcium from bones.

Appreciation for Vitamin D's non calcium-related biological activities began in 1979, with Stumpf's discovery that radioactive Vitamin D localizes to many tissues not associated with calcium metabolism (*Science* 206:1188–1190, 1979). In 1981, Abe et al. reported that mouse myeloid leukemia cells possessed VDR, and that their exposure to Vitamin D led to terminal differentiation (*PNAS USA* 78:4990–4994, 1981). Since then VDR has been described in carcinomas of the prostate, breast, colon, lung, pancreas, endometrium, bladder, cervix, ovaries, squamous cell carcinoma, renal cell carcinoma, myeloid and lymphocytic leukemia, medullary thyroid carcinoma, melanoma, multiple myeloma, retinoblastoma, and sarcomas of the soft tissues and bone.

In vitro assays using 1,25 dihydroxyvitamin D or its analogues demonstrated antiproliferative effects in cell lines derived from many malignancies including adenocarcinomas of the prostate (*Molec. and Cell. Endocrinology* 126:83–90, 1997; *Proc. Amer. Assoc. Cancer Res.* 38:456, 1997; *J. Ster. Biochem. and Molec. Biol.* 58:277–288, 1996; *Endocrinology* 137:1551561, 1996; *Endocrinology* 136:20–26, 1995; *Cancer Research* 54:805–810, 1994; *Endocrinology* 132:1952–1960, 1993; and *Anticancer Research* 14:1077–1081, 1994), breast (*Proc. Amer. Assoc. Cancer Res.* 38–456, 1997; *Biochemical Pharmacology* 44:693–702, 1992); colon (*Biochemical and Biophysical Research Communications* 179:57–62, 1991; *Archives of Pharmacology* 347:105–110, 1993); pancreas (*British Journal of Cancer* 73:1341–1346, 1996); and endometrium (*Journal of Obstetrics and Gynaecology Research* 22:529–539, 1996); lung (*Anticancer Research* 16:2953–2659, 1996); myeloid leukemia (*PNAS USA* 78:4990–4994, 1981); melanoma (*Endocrinology* 108:1083–1086, 1981); and sarcomas of the soft tissues (*Annals of Surgical Oncology* 3:144–149, 1996) and bone (*Journal of the Japanese Orthopaedic Association* 69:181–190, 1995).

Studies in animals have shown antiproliferative activity of Vitamin D or its analogues in prostate cancer (*Urology* 46:365–369, 1994); breast cancer (*J. NCI* 89:212–218, 1997; *Lancet* 1:188–191, 1989); squamous cell carcinoma (*Molecular and Cellular Differentiation* 3:31–50, 1995); myeloid leukemia (*Blood* 74:82–93, 1989 and *PNAS USA* 80:201–204, 1983) and retinoblastoma (*Archives of Opthalmology* 106:541–543, 1988; *Archives of Opthalmology* 106:536–540, 1988). The mechanism of Vitamin D's antiproliferative effects remains unknown, although it has been proposed that Vitamin D increases synthesis of TGF-β1 and TGF-β2, decreases the expression of epidermal growth factor receptors, leads to dephosphorylation of the retinoblastoma protein, induces cell cycle arrest in G1, perhaps by induction of the cyclin dependent kinase inhibitors p21 (waf1) and p27(kip1), and induces the production of insulin-like growth factor binding protein.

The patent literature is replete with attempts to treat tumors with Vitamin D compounds. U.S. Pat. No. 4,391,802 disclosed treating leukemioid diseases with 1α-hydroxy Vitamin D derivatives. The use of 1α-hydroxy derivatives with a 17 side chain greater in length than the cholesterol or ergosterol side chains was disclosed in U.S. Pat. No. 4,717,721. Additional Vitamin D analogs are described in U.S. Pat. No. 4,851,401 (cyclopentano-Vitamin D analogs), U.S. Pat. No. 4,866,048, U.S. Pat. No. 5,145,846 (Vitamin $D_3$ analogs with alkynyl, alkenyl, and alkanyl side chains), U.S. Pat. No. 5,120,722 (trihydroxycalciferol), U.S. Pat. No. 5,547,947 (fluoro-cholecalciferol compounds), U.S. Pat. No. 5,446,035 (methyl substituted Vitamin D), U.S. Pat. No. 5,411,949 (23-oxa-derivatives), U.S. Pat. No. 5,237,110 (19-Nor-Vitamin D compounds), U.S. Pat. No. 4,857,518 (hydroxylated 24-homo-Vitamin D derivatives). Additional Vitamin D analogs are shown in U.S. Pat. Nos. 4,804,502; 5,374,629; 5,403,940; 5,446,034; and 5,447,924.

Few attempts have been made to test Vitamin D's antiproliferative effects in humans with cancer. Koeffler et al., *Cancer Treatment Reports* 69:1399–1407, 1985, gave 2 mcg of 1,25-dihydroxyvitamin D daily for 8 weeks or longer to 18 patients with myelodysplastic syndrome. Eight of 18 patients had minor and transient improvements in the peripheral blood counts, but by the end of the 12 week study no patient showed significant improvement and 4 patients experienced symptomatic hypercalcemia. Bower et al., *Lan-* cet 337:701–702, 1991, treated 19 patients with locally advanced or cutaneous metastatic breast cancer with topical calcipotriol, a Vitamin D analogue. Three of the 14 patients who completed 6 weeks of treatment showed a 50% reduction in the bidirectional diameter of the treated lesions and one other patient showed minimal response, however hypercalcemia was a complication of the treatment. Palmieri-Sevier et al., *Am. J. Medical Sciences* 306:309–312, 1993, reported a case of long term remission of parathyroid carcinoma which appeared to be induced and maintained by Vitamin D therapy. Rustin et al., *Brit. J. Can.* 74:1479–1481, 1996, performed a clinical trial with a continuous dose of calcitriol in patients with ovarian cancer, and again encountered hypercalcemia.

A phase II trial of oral 1,25-dihydroxyvitamin D (calcitriol) in hormone refractory prostate cancer was reported by Osborn et al., *Urol. Oncol.*, 1:195–198, 1995. Fourteen patients were given a daily oral dose of 0.5–1.5 mcg calcitriol, but no significant response was demonstrated, and clinical deterioration was documented in most of the patients. Thirteen of the patients experienced hypercalcemia, which is the most common side effect of treatment with Vitamin D and its analogs. Concern that hypercalcemic effects of Vitamin D would preclude the achievement of therapeutic, anti-neoplastic serum levels has inhibited the study of the use of this vitamin in humans with cancer. It is an object of this invention to provide a method of treatment with Vitamin D drugs (such as calcitriol) that avoids such hypercalcemia, while permitting the use of this class of drugs in the treatment of tumors and other hyperproliferative diseases.

SUMMARY OF THE INVENTION

Vitamin D and its analogs can be administered in accordance with the present invention, for the treatment of neoplastic diseases, such as the types of tumors mentioned above, which are responsive to treatment with Vitamin D drugs. The method can also be used to treat hyperproliferative skin diseases, such as psoriasis, disorders of keratinization and keratosis, or disorders of sebaceous glands, such as acne or sebonheic dermatitis. The method includes administering to the subject a therapeutically effective pulsed dose of the Vitamin D drug in a sufficient amount to have a therapeutic effect, without inducing hypercalcemia, particularly symptomatic hypercalcemia, for example grade 3 or stage 4 hypercalcemia. This treatment is especially effective to allow the use of highly calcemic drugs (such as drugs having a calcemic index of 0.5 or more) which are often highly effective in the treatment of tumors and hyperproliferative diseases, but which have been avoided in the past because of their calcemic side effects. The dosing regimen of the present invention for the first time allows therapeutically effective antiproliferative (and particularly antineoplastic) amounts of these drugs to be given without inducing the dangerous side effect of life-threatening hypercalcemia, while surprisingly having a prolonged therapeutic specific anti-tumor or general antiproliferative effect.

In a first disclosed embodiment, the Vitamin D drug is administered to a subject having a neoplasm that expresses a Vitamin D receptor, and responds to treatment with a Vitamin D drug. Particular types of tumor that respond to such treatment include adenocarcinomas of the prostate, breast, colon, pancreas and endometrium, as well as small cell and non-small cell cancer of the lung (including squamous, adenocarcinoma and large cell types), squamous cell carcinoma of the head and neck, transitional cell cancer of the bladder, ovarian and cervical (e.g. squamous cell carcinoma) cancer, renal cell carcinoma, myeloid and lymphocytic leukemia, lymphoma, medullary thyroid carcinoma, melanoma, multiple myeloma, retinoblastoma, and sarcomas of the soft tissues and bone. In particular embodiments, the neoplasm is adenocarcinoma of the breast or prostate.

In yet other specific embodiments, the Vitamin D drug is one that would induce hypercalcemia (particularly symptomatic or life-threatening hypercalcemia) in a subject to which the drug is given at antiproliferative doses. The method would have particular application to drugs that are as calcemic as calcipotriol (calcemic index of about 0.005–0.01), 11α-fluoromethyl-1α,25-(OH)$_2$-D$_3$ (having a calcemic index of about 0.1), and drugs having a calcemic index greater than 0.5, for example greater than or equal to 1 (the calcemic index of calcitriol). Drugs with which the method is particularly useful are those drugs having a half-life no greater than about 1 day, for example no greater than about 6 hours, when the dose is given as a therapeutically effective dose. These half-lives are sufficiently short that they allow the blood level to return to non-calcemic levels for a sufficient period between doses so that full osteoclast activation does not occur. In particular embodiments, blood levels of calcium return to normal between doses. The Vitamin D drug is administered in an amount that raises a serum level of Vitamin D in the subject with a tumor to a supraphysiologic amount for a sufficient period of time to induce differentiation or regression of the tumor without causing symptomatic hypercalcemia.

For example, where the Vitamin D analog is calcitriol, it can be administered in a high pulse dose no more than once every three days, for example once a week. Although calcitriol has been used in the past to treat cancer, dosages of such regimens have been 0.5–1.5 mcg per day for prolonged periods of time, which has caused symptomatic hypercalcemia. In accordance with some embodiments of the present invention, calcitriol is orally administered in a dose of at least 0.12 mcg/kg per day (8.4 mcg in a 70 kg person) no more than once every 5 or 6 days, for example once a week. In certain examples, the drug is administered no more than once every three days, or no more than once per week. Even higher doses of calcitriol are possible using the pulsed dose regimen of the present invention, for example administering the calcitriol orally in a dose of at least about 0.48 mcg/kg per day, for example 1 mg/kg per day or higher, e.g. 2–3 mg/kg per day, no more than once per week. As the dosage of the calcitriol or other Vitamin D drug increases, the interval between doses can be increased (for example to as long as 7–10 days) to avoid symptomatic hypercalcemia. It has surprisingly been observed that pulsed increases in the blood level of Vitamin D are sufficient to have an anti-tumor or antiproliferative effect for a prolonged period of time (e.g. 10 days), so that the dosing regimen of the present invention can be followed while encountering a lowered risk of hypercalcemia.

The invention also includes a pharmaceutical composition comprising a Vitamin D drug in a pharmaceutical dosage form containing at least 5 micrograms (mcg) of calcitriol, for example 5–100 mcg. The dosage form may be an oral, intravenous, intramuscular, topical, subcutaneous, transdermal, sublingual, intranasal, intratumoral or other preparation, but in particular disclosed embodiments the pharmaceutical dosage form is an oral dosage form, such as a tablet or capsule.

The foregoing and other objects, features, and advantages of the invention will become more apparent from the following detailed description of several preferred embodiments.

DETAILED DESCRIPTION OF SEVERAL EMBODIMENTS

Definitions

Figure 1:
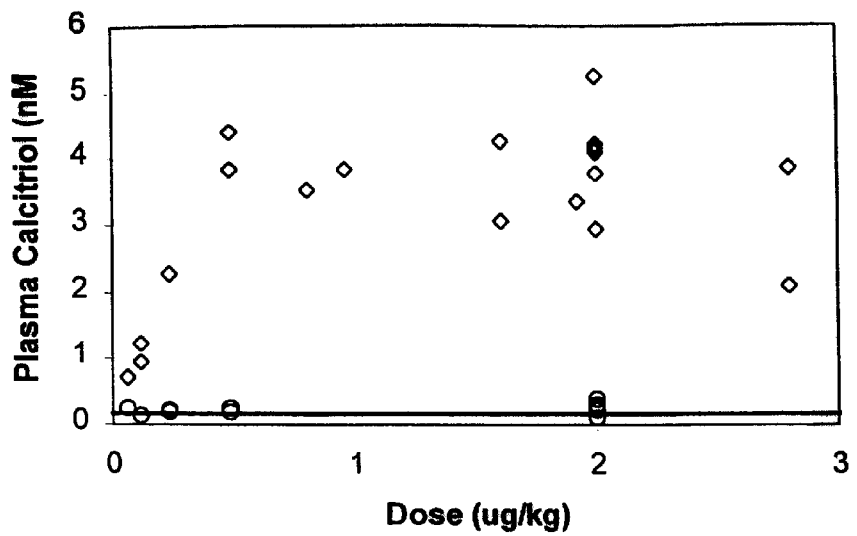
FIG. 1 is a diagram showing peak and trough plasma calcitriol levels in subjects who received the indicated dose of calcitriol over four hours. Peak levels (O) were determined at 6 hours after administration, and trough levels (O) were determined at 48 hours after administration.

The following definitions will help with an understanding of the terms used in this specification.

A "Vitamin D drug" is a drug that raises the blood or tissue level of Vitamin D, or has an affinity for the Vitamin D receptor, for example binding to that receptor with a Relative Competitive Index (RCI) of 0.05 or greater, more particularly 5 or greater, for example 5–250. The RCI is indexed to an RCI of 100 for calcitriol. The term also includes any of the family of secosteroids with antirhichitic activity, such as Vitamin $D_2$ (ergocalciferol) and Vitamin $D_3$ (cholecalciferol), their precursor molecules such as ergosterol (7-dehydro-22-dehydro-24-methyl-cholesterol) and 7 dehydrocholesterol, 25-hydroxyvitainin $D_3$, the 3-hydroxylated dihydrotachysterol$_2$, the 1α-hydroxylated alfacalcidol (1α-hydroxyvitamin $D_3$) and calcitriol (1α, 25-dihydroxyvitamin $D_3$), as well as the numerous natural and synthetic Vitamin D analogs set forth in the attached Appendix 1 (from Bouillon et. al, *Endocrine Reviews* 16: 200–257,1995).

Vitamin D drugs also include Vitamin D preparations and analogs that are currently in clinical use, such as Rocaltrol® (Roche Laboratories), Calcijex®unjectable calcitriol, investigational drugs from Leo Pharmaceutical including EB 1089 (24a,26a,27a-trihomo-22,24-diene-1α, 25-$(OH)_2$-$D_3$), KH 1060 (20-epi-22-oxa-24a,26a,27a-trihomo-1α,25-$(OH)_2$-$D_3$), MC 1288 and MC 903 (calcipotriol), Roche Pharmaceutical drugs that include 1,25-$(OH)_2$-16-ene-$D_{3, 1,25}$-$(OH)_2$-16-ene-23-yne-$D_3$, and 25-(OH)2-16-ene-23-yne-$D_3$, Chugai Pharmaceuticals 22-oxacalcitriol (22-oxa-1α,25-(OH)2-$D_3$; 1α-$(OH)D_5$ from the University of Illinois; and drugs from the Institute of Medical Chemistry-Schering AG that include ZK 161422 and ZK 157202. Appendix 3 provides additional information about chemical structure, route of administration and dosing of some of these compounds. Vitamin D analogs also include topical preparations of Vitamin D, such as Calcipotriene (Dovonex) and Tacalcitol, used in the treatmnent of psoriasis.

A "Vitamin D receptor" (or VDR) is a protein transcription factor, for which the gene and its product have already been characterized and found to contain 427 amino acids, with a molecular weight of about 47,000, or variants thereof The fall length cDNA of the human VDR is disclosed in Baker et al., *PNAS, USA* 85:3294–3298, 1988.

"Tumor cells that express (or contain) the Vitamin D receptor" are those tumors that have been shown to contain the Vitamin D receptor, tumors that are subsequently shown to contain the receptor (using inununohistochemical or other techniques), tumor types (such as breast cancer) that have demonstrated a clinical improvement in response to treatment with calcitriol or its analogs or other Vitamin D drugs, and tumors for which there is epidemiologic data demonstrating an association between low Vitamin D levels and higher cancer incidence (such as adenocarcinomas of the prostate, breast and colorectum). The presence of Vitamin D receptors can be determined by any means known in the art, such as any of the techniques disclosed in Pike, *Ann. Rev. Nut* 11:189–216, 1991.

"Elevated (or supraphysiologic) level of Vitamin D" refers to a 1,25-dihydroxyvitamin D plasma concentration greater than about 0.15 nM (65 pg/ml), or other Vitamin D concentration greater than normal in the laboratory where the concentration is measured, for example in humans a total human plasma concentration greater than about 10 ng/ml of 25-hydroxyvitanin D (although this and all other normal values can vary depending on the techniques used to measure the concentration).

"Hypercalcemia" refers to a calcium plasma concentration greater than normal in the laboratory where the concentration is measured, for example greater than about 10.5 mg/dL in humans (although this and all other normal values can vary depending on the techniques used to measure the concentration). Hypercalcemia can be broken into grades 0–4, as set forth in Appendix II.

"Symptomatic hypercalcemia" refers to laboratory demonstrated hypercalcemia associated with one of more of the signs or symptoms of hypercalcemia. Early manifestations of hypercalcemia include weakness, headache, somnolence, nausea, vomiting, dry mouth, constipation, muscle pain, bone pain, or metallic taste. Late manifestations include polydypsia, polyuria, weight loss, pancreatitis, photophobia, pruritis, renal dysfunction, aminotransferase elevation, hypertension, cardiac arrhythmias, psychosis, stupor, or coma. Ectopic calcification has been reported when the calcium-phosphate product (multiplying the concentrations of calcium and phosphate) exceeds 70. "Severe symptomatic hypercalcemia" refers to grade 3 or grade 4 hypercalcemia.

A "tumor" is a neoplasm, and includes both solid and non-solid tumors (such as hematologic malignancies). A "hyperproliferative disease" is a disorder characterized by abnormal proliferation of cells, and generically includes skin disorders such as psoriasis as well as benign and malignant tumors of all organ systems. "Differentiation" refers to the process by which cells become more specialized to perform biological functions, and differentiation is a property that is totally or partially lost by cells that have undergone malignant transformation.

A "therapeutically effective dose" is a dose which in susceptible subjects is sufficient to prevent advancement, or to cause regression of the disease, or which is capable of relieving symptoms caused by the disease, such as fever, pain, decreased appetite or chachexia associated with malignancy.

A "pulse" dose of a Vitamin D drug refers to administration of the drug in a sufficient amount to increase the blood or tissue level of the Vitamin D drug to a supraphysiologic concentration for a sufficient period of time to have a therapeutic benefit, but with a sufficient period between doses to avoid hypercalcemia, given the pharmacological half life of the drug, its rate of elimination from the body, and its calcemic index.

The "calcemic index" of a drug is a measure of the relative ability of a drug to generate a calcemic response, for example as measured and reported in Bouillon et al., *Endocrine Reviews* 16:200–257, 1995. A calcemic index of 1 corresponds to the relative calcemic activity of calcitriol. A calcemic index of about 0.01 corresponds to the calcemic activity of calcipotriol. A calcemic index of 0.5 would correspond to a drug having approximately half the calcemic activity of calcitriol. The calcemic index of a drug can vary depending on the assay conducted, e.g. whether measuring stimulation of intestinal calcium absorption (ICA) or bone calcium mobilizing activity (BCM), as reported in Hurwitz et al., *J. Nutr* 91:319–323, 1967 and Yamada et al., Molecular, *Cellular and Clinical Endocrinology* (Berlin), pages 767–774, 1988. Hence relative calcemic activity is best expressed in relation to the calcemic activity of calcitriol, which is one of the best characterized Vitamin D drugs.

Vitamin D Drugs

Normal serum levels of 1,25-dihydroxyvitamin D range between 0.05 and 0.16 nM, however therapeutic drug levels necessary for cancer inhibition have not been well defined. Skowronski et al. (*Endocrinology* 136-20-26, 1995) demonstrated measurable growth inhibition of LNCaP human prostate cancer cells in vitro at a 1,25-dihydroxyvitamin D concentration of 0.1 nM and 50% growth inhibition at a 1.0 nM concentration. Peehl et al. (*Cancer Research* 54:805–810, 1994) incubated human prostate cancer cells in primary culture with 1,25-dihydroxyvitamin D concentrations ranging between 0.025 and 25 nM and demonstrated half maximal growth inhibition at levels between 0.25 and 1.0 nM. Previous clinical trials of Vitamin D in the treatment of cancer have proceeded on the assumption that high levels of the drug were needed for a prolonged period of time to have a therapeutic benefit. The inventors of the present invention, however, have surprisingly shown that intermittent supraphysiologic levels of 1,25-dihydroxyvitamin D (for example greater than or equal to 0.25 nM) are sufficient to inhibit cancer growth and other proliferative disease in mammals. This surprising finding now permits the therapeutic benefits of Vitamin D therapy to be achieved without substantial risk of morbidity from iatrogenic hypercalcemia induced by the therapy.

Calcitriol is a short acting preparation of 1,25-dihydroxyvitamin D, which therefore offers an opportunity for intermittent treatment aimed at achieving high serum 1,25-dihydroxyvitamin D levels for brief periods of time. This regimen has surprising anti-tumor activity, while minimizing toxicity, such as hypercalcemia. Calcitriol has primarily been studied when chronically administered as replacement therapy, for which its usual dose is 0.25–1.0 mcg per day. Peak serum concentration is reached at 2 hours and serum half life is 3–6 hours. Intestinal absorption of calcium begins to increase 2 hours after administration. Hypercalcemic effect is maximal at 10 hours and lasts 3–5 days.

In one embodiment of the invention, a sufficient dose of calcitriol is administered to raise serum 1,25-hydroxyvitamin D levels to a therapeutically effective level for a pulsed dose that has an anti-proliferative effect without causing significant hypercalcemia (for example symptomatic grade 3 or grade 4 hypercalcemia). With calcitriol, an example of such a dose would produce a serum level of at least about 0.5 nM, for example about 0.9 nM or more (e.g. 1–25 nM, for example 5–10 nM), for at least 2 hours (e.g. 2–5 hours) and preferably no more than 6 hours. In particular embodiments, the pulsed dose of calcitriol does not exceed a dose at which symptomatic hypercalcemia occurs, or more preferably a pulsed dose at which even laboratory hypercalcemia occurs.

Information about short term effects of higher than replacement doses of calcitriol is available for helping predict drug effects. Papapoulus et al., (*Clinical Science* 62:427429, 1982) gave 2 mcg of calcitriol as a single oral dose to healthy volunteers and achieved peak 1,25-dihydroxyvitamin D sernm concentrations of 0.235 and 0.351 nM. Mason et al. (*BMJ* 1980:449–450) gave a single oral dose of 4 mcg calcitriol to healthy volunteers and achieved peak 1,25-dihydroxyvitamin D serum concentrations of 0.42 nM with no elevation in serum calcium. Brickinan et al. (*Am. J. Med.* 57:28–33, 1974) treated normal volunteers with calcitriol doses up to 2.7 mcg/day for 7 to 15 days. While calcium absorption and excretion were increased, no significant elevations in serum calcium were observed. Adams et al. (*Kidney Int.* 21:90–97, 1982) treated normal volunteers with up to 3 mcg/day of calcitriol for 6–12 days and achieved stable 1,25-dihydroxyvitamin D serum levels of 0.184–0.235 nM. None of the patients who were on a low calcium diet experienced elevation in serum calcium. Geusens et al. (*Calcifed Tissue Int.* 49:168–173, 1991) gave 4 mcg of calcitriol per day for 4 days to 27 postmenapausal women with osteoporosis or osteoarthritis. They demonstrated increased urinary calcium excretion but no increase in urinary hydroxyproline excretion. Four of the 27 patients had a serum calcium above 10.8 but no clinically significant hypercalcemia was observed.

Antiproliferative levels of 1,25-dihydroxyvitamnin D can be achieved for short periods of time with minimal adverse effects, particularly if hypercalcemia during short course 1,25-dihydroxyvitamin D therapy is primarily mediated by increases in intestinal calcium absorption (slower calcium elevation) rather then osteoclast activation (which can rapidly mobilize calcium from bone). Higher 1,25-dihydroxyvitamin D levels are achievable when the drug is given in conjunction with a reduced calcium diet to minimize intestinal calcium absorption, and adequate hydration to maximize calcium excretion. The maximal tolerated dose of calcitriol, when given intermittently has not been defined, but doses as high as 0.48 mcg/kg have been tolerated without hypercalcemia.

Higher doses of a Vitamin D drug, sufficient to achieve therapeutic antiproliferative levels, may also be achieved by administering the drug in conjunction with bisphosphonate osteoclast inhibitors, such as pamidronate. Selby et al. (*Endocrinology* 108:1083–1086, 1981) provided an example of treating hypercalcemia due to Vitamin D with pamidronate. The potential for achieving high serum 1,25-dihydroxyvitamin D levels when osteoclasts are inhibited in patients with osteopetrosis is possible with calcitriol doses as high as 32 mcg/day for 3 months (Key et al., *NEJM* 310:409415, 1984) where stable serum levels of 1,25-dihydroxyvitamin D peaked at 2.32 nM with no hypercalcemia.

The following Examples illustrate the general method of the present invention, as well as specific case histories to illustrate its use. These Examples also provide a general framework for evaluating other Vitamin D drugs, and determining a therapeutically effective dose of a Vitamin D drug in a subject with a Vitamin D responsive hyperproliferative disease, without inducing symptomatic iatrogenic hypercalcemia.

EXAMPLE 1

General Treatment Plan

A patient with a known Vitamin D receptor positive tumor (such as adenocarcinoma of the prostate, breast, lung, colon or pancreas, or transitional cell carcinoma of the bladder, or melanoma) may be placed on a prescribed reduced calcium diet prior to treatment, to help minimize intestinal absorption and allow even higher doses of the Vitamin D drug to be used. This reduced calcium diet may be continued for the duration of treatment, and for one week after the last dose of the Vitamin D drug. The diet ideally restricts daily calcium intake to 400–500 mg, by avoiding all dairy products, as well as sardines and other fish canned with their bones, legumes, greens, and any calcium fortified foods or drinks. The subject is then asked to drink 4–6 cups of fluid more than usual intake starting 12 hours before treatment and continuing for days 1, 2, and 3, to assure adequate oral hydration. Magnesium containing antacids, oral calcium supplements, cholestyramine, colestipol, and other bile resin binding agents may also be avoided during treatment.

Baseline laboratory tests that may be obtained include serum levels of calcium, phosphate, and 1,25-dihydroxyvitamin D. At the initial dose level, e.g. calcitriol 0.06 mcg/kg po (or another Vitamin D drug for which the dose is to be determined) is divided into 4 doses, and one of those four doses is taken during each hour for 4 hours until the total 0.06 mcg/kg dose is taken. Alternatively, a single higher dose formulation may be ingested. The doses may be rounded up to the nearest 0.5 mcg. The subject is monitored daily for symptoms of hypercalcemia for at least 2–3 days following administration.

The patient may have a variety of laboratory tests performed to monitor the presence of hypercalcemia, or any physiological consequences of hypercalcemia. Such tests may include calcium at 0, 24, 48 hours, and baseline levels of creatinine, total billirubin, ALT, alkaline phosphatase, and a complete blood count. Other possible laboratory tests include phosphate, 1,25-dihydroxyvitamin D levels at 0, 6, 24, 48 hours, and 24 hour urine collection for calcium and hydroxyproline on day 2. Subjects are treated with the once a week pulse dose of Vitamin D weekly until disease progression or 4 weeks, whichever comes first, and are followed for 2 months from enrollment. If Grade 3 toxicity is encountered, the treatment is stopped.

An initial dose may be chosen from safe doses documented in the literature, followed by a multistage escalation scheme, such as the one described by Gordon and Willson (*Statistic in Medicine* 11:2063–2075, 1992). Patient accrual occurs in stages I, II, and III. The stages require the accrual of one, three, or six patients respectively before dose escalation. All patients enrolled at a dose level complete 4 weeks of treatment before the dose level is escalated. In stage I, a single patient is entered at each dose level. Accrual continues in stage I until the first Grade 3 toxicity is encountered. When a Grade 3 toxicity is encountered, two more patients are accrued at the same dose level and accrual will continue in stage II. Doses are reduced one level if one Grade 4 or 5 toxicity is encountered in stage I.

Accrual continues in stage II if no Grade 3 toxicities are encountered. When one or two Grade 3 or Grade 4 toxicities are encountered, three additional patients are accrued at the same dose level and accrual continues in stage III. Doses are reduced one level if one Grade 5 or three Grade 3 or Grade 4 toxicities are encountered in stage II. In stage III six patients are enrolled at each dose level. If only one Grade 3 toxicity is encountered, the dose will be escalated and the accrual will revert to stage II. If two or more Grade 3 or greater toxicities occur, no finther escalation will occur. The MTD (maximum tolerated dose) is defined asthat dose at which ⅓ or fewer of the subjects experience grade 3 toxicity. For calcitriol, the initial dose was 0.06 mcg/kg po over 4 hours. At each successive level, the dose is doubled until the first grade 3 toxicity is encountered. After that, each dose increase is 1.33× of the preceding level according to a modified Fibonacci scheme (Dillman and Koziol, *Molecular Biotherapy* 4:117–121, 1992).

For calcitriol, the pulse dose was given to each subject weekly, and the subject was monitored for early signs and symptoms of hypercalcemia, such as weakness, headache, somnolence, nausea, vomiting, dry mouth, constipation, muscle pain, bone pain, metallic taste. The patient was also monitored for any more serious manifestations, such as polydypsia, polyuria, weight loss, pancreatitis, photophobia, pruritis, renal dysfunction, aminotransferase elevation, hypertension, cardiac arrhythmias, psychosis, stupor, coma, and ectopic calcification. Appropriate treatment is instituted for any patient who demonstrates hypercalcemic toxicity, and the calcitriol is stopped until serun calcium returns to normal.

The following Table I illustrates a protocol that can be followed with each drug to determine a tolerated pulse dose. A protocol for determining a therapeutic dose will be described in Example 2.

TABLE 1

Example of Protocol for Determining Tolerated Dose

| | | WEEKS 1–4 | | | WEEKS 5–8 | | | |
| | | | | | Follow-Up | | Premature | |
| Evaluation & Procedures | EVALUATION Screen | Day 1 | Day 2 | Day 3 | Week 5 | Week 7 | Until Ca nl daily | After Ca nl every 2 |
| --- | --- | --- | --- | --- | --- | --- | --- | --- |
| Informed Consent | x | | | | | | | |
| Inclusion / Exclusion Criteria | x | | | | | | | |
| Physical Exam | x | x | | | | x | x | |
| Sitting Vital Signs | x | x | | | | | x | |
| Adverse Effects Recorded | | | x | x | x | x | x | x |
| Calcitriol administered | | x | | | | | | |
| Calcium | x | x | x | x | x | x | x | x |
| Phosphate | x | x | x | x | | | x | |
| 1,25-dihydroxyvitamin D level | x | xx | x | x | | | x | |
| Creatinine | x | x | | | | | x | |
| Total Bilirubin | x | x | | | | | x | |
| ALT | x | x | | | | | x | |
| Alkaline Phosphatase | x | x | | | | | x | |
| Albumin | x | | | | | | | |

TABLE 1-continued

Example of Protocol for Determining Tolerated Dose

| | | WEEKS 1–4 | | | WEEKS 5–8 | | | |
| --- | --- | --- | --- | --- | --- | --- | --- | --- |
| | | | | | Follow-Up | | Premature | |
| Evaluation & Procedures | EVALUATION Screen | Day 1 | Day 2 | Day 3 | Week 5 | Week 7 | Until Ca nl daily | After Ca nl every 2 |
| Complete Blood Count | x | x | | | | | | |
| β-hCG (select patients) | x | | | | | | | |
| Urine Collection | x | | x | | | | | |
| Diet Questionnaire | | x | | | | | | |
| Tumor measurements (when appropriate) | x | | | | | x | | |

EXAMPLE 2

Determination of Therapeutically Effective Dose

Tumor markers, such as PSA, CA 15-3, and others can be used to assess tumor progression or regression, although the results of such assays can sometimes be difficult to interpret because administration of Vitamin D has been shown to increase tumor marker production while inhibiting cancer cell growth. This effect is presumably due to the differentiation inducing properties of Vitamin D.

Alternative means for determining a therapeutic response can also be employed, for example direct radiographic measurement of tumor lesions. A measurable lesion may be considered one that is bidimensionally measurable, with clearly defined margins on physical exams, x-ray, or scan. At least one diameter is preferably greater than 0.5 cm. Bone lesions are not included.

Evaluable disease includes unidimensionally measurable lesions, masses with margins not clearly defined, palpable nodal disease, lesions with both diameters less than 0.5 cm, and bone disease. Non-evaluable disease includes disease manifested by pleural effusions, ascites, or disease documented by indirect evidence only (e.g., by lab values which fall into a category of not being evaluable). The objective status is recorded at entry into the trial and during week 7 (where week 1 is the week during which the first dose of the Vitamin D drug is given). If an organ has too many measurable lesions to measure at each evaluation, a specific number (such as three lesions) are selected to be followed before the patient is entered in the study.

A complete response (CR) is the complete disappearance of all measurable and evaluable disease, with no new lesions. If the subject has effusions, ascites or disease assessable by surgical restaging (e.g., testicular and extragonadal gem cell cancer), the disease must be cytologically negative. Patients with markers or indirect evidence of involvement must have normalization of abnormal values. All measurable, evaluable and non-evaluable lesions and sites must be assessed. A partial response (PR) is found in subjects with at least one measurable lesion with 50% decrease of perpendicular diameters of all measurable lesions, with no progression of evaluable disease, and no new lesions. All measurable and evaluable lesions and sites must be assessed. In lung cancer, a greater than 50% decrease in estimated area of evaluable, but non-measurable, tumor mass, as agreed upon by two independent observers, not to include pleural effusions. Stabilization is a response that does not qualify as a complete response, partial response or progression.

EXAMPLE 3

Treatment of Breast Cancer

In this example, a 42 year old woman with breast carcinoma metastatic to numerous sites in the skeleton received a dose of 11 mcg of calcitriol (Rocaltrol, Roche) administered as 2–2 tablets (0.5 mcg each tablet) divided into four nearly equal doses given in hour one, two, three and four. The patient received this same therapy on day 1, 8, 15 and 22, and then was observed on study until day 56, and tolerated the treatment well. She had no Grade II or higher toxicities on the NCI toxicity grading scale (Appendix 2). Subjective beneficial effects observed included a reduction in pain and in analgesia required. Objective benefits included a progressive decrease in the serum tumor marker CA15-3 from 445 (pre-treatment) to 365 (day 27), 365 (day 48) and 320 (day 70). Radiologic evaluation of areas of known bony involvement showed progressive sclerosis of multiple lesions in the pelvis and right hip, indicating bone healing as a positive response to therapy. No new lesions or pathologic fractures identified were identified by day 64.

EXAMPLE 4

Treatment of Melanoma

In this example a 72 year old man with metastatic malignant melanoma of the right jaw received a dose of 37 mcg of calcitriol (Rocaltrol, Roche) administered as 74 tablets (0.5 mcg each tablet) divided into four nearly equal doses given in hour one, two, three and four. The patient received this same therapy on day 1, 8, 15 and 22, and observed until at least day 56. The level of calcitriol in a plasma sample obtained two hours after the last dose of calcitriol (on week one) was determined using a commercial assay at Endocrine Sciences, Inc. The level was 1826 pg/ml, compared to the range for calcitriol levels in normal controls being 21 to 65 pg/ml. In spite of the markedly elevated levels of calcitriol achieved with this weekly schedule, this patient did not have any subjective or objective toxicity. Levels of serum calcium and other chemical and hematological parameters in the blood remained normal.

EXAMPLE 5

Summary of Trial Results

Patients

Eligibility criteria included histologically confirmed malignancy refractory to standard therapy; age $\geq 18$ years; expected survival of >2 months; ECOG performance status $\leq 2$; hematocrit $\geq 30$; serum creatinine $\leq 1.2$ mg/dL; serum calcium ≦10.5 mg/dL; serum phosphate <4.2 mg/dL; ALT ≦60 IUIL; total serum bilirubin <2 mg/dL. Exclusion criteria included pregnancy, history of hypercalcemia, kidney stones, heart failure or significant heart disease including myocardial infarction in the last 3 months, known cardiac ejection fraction less than 30%, current digoxin therapy, thiazide diuretic therapy within 7 days, bisphosphonate treatment within 4 weeks, systemic steroid therapy within 2 weeks, and unwillingness or inability to stop all magnesium containing antacids, bile resin binding drugs, or calcium supplements for the duration of the study.

Treatment

Baseline evaluation included a complete history and physical exam, complete blood count, serum creatinine, serum calcium, serum phosphate, total serum bilirubin, ALT, alkaline phosphatase, albumin, serum β-hCG in women of childbearing potential, 24 hour urine collection for calcium, and tumor measurements.

Patients were asked to maintain a reduced calcium diet for the four treatment weeks, with a goal of less than 500 mg per day, as described in Example 1. Calcitriol (Rocaltrol®, Roche Pharmaceuticals) was given orally once a week for four weeks. Each weekly dose was given in four divided doses given hourly over four hours. The starting dose was 0.06 μg/kg.

Monitoring

Complete blood count, serum creatinine, total serum bilirubin, ALT, alkaline phosphatase were monitored weekly. Serum calcium and phosphate were checked on the treatment day (day 1), and on days 2 and 3. Twenty-four hour urinary calcium excretion was measured on day 2. The 1,25-dihydroxyvitaunin D levels were measured by $^{125}I$ radioimmunoassay (Incstar, Stillwater, Minn.) and by a radioreceptor assay using calf thymus 1,25-dihydroxyvitamin D receptor (Endocrine Sciences, Calabasas Hills, Calif.). Peak levels were measured two hours after all the pills had been ingested. Trough levels were measured approximately 48 hours later.

Compliance with the diet was monitored with a seven day dietary recall questionnaire directed at calcium rich foods. Daily calcium intacke was estimated by adding the calcium content of calcium rich foods identified by the questionnaire to the estimated calcium content of the basal diet. The calcium content of the basal diet was calculated to be 1 mg of calcium/8 Kcal. Caloric intake was estimated with the use of the Food Processor 7.0 software (ESHA Research, Salem, Oreg.).

After completing the four week treatment period, patients were monitored for four additional weeks. Serum calcium was checked in weeks 5 and 7 and tumor measurements were obtained in week 7. All toxicities were graded according to NCI Common Toxicity Criteria. Response was assessed according to WHO guidelines.

Statistical Considerations

The planned dose escalation was governed by the multistage escalation scheme described by Gordon and Willson, 1992. The maximal tolerated dose (MTD) was defined as that dose at which ⅓ or fewer of the patients experienced Grade 3 toxicity (64). Patients who had evidence of response or stable disease, and no Grade 3 or greater toxicity were permitted to reenroll and receive either the same dose or the next higher dose of calcitriol. Statistical analysis was performed using StatView 5.0 for Windows software (SAS Institute, Cary, N.C.)

RESULTS

Fifteen different patients were enrolled in 20 cycles of therapy (Table 2). Two patients were withdrawn from the study prior to completion of the four week regimen because of disease progression. No patient withdrew because of toxicity of therapy or unacceptability of the diet. Five patients reenrolled for a second cycle of treatment.

TABLE 2

Individual Patients Enrolled on Study

| Patient | Age | Gender | Malignancy | Cycle 1 dose (μg/kg) | Cycle 2 dose (μg/kg) |
|---|---|---|---|---|---|
| 1 | 79 | male | Adenocarcinoma of the prostate | 0.06 | 0.12 |
| 2 | 42 | female | Adenocarcinoma of the breast | 0.12 | |
| 3 | 70 | male | Adenocarcinoma of the lung | 0.24 | |
| 4 | 72 | male | Melanoma | 0.48 | |
| 5 | 53 | male | Squamous Cell of the tonsil | 0.48 | |
| 6 | 48 | female | Hepatocellular carcinoma | 0.80 | 1.60 |
| 7 | 80 | male | Adenocarcinoma of the prostate | 0.96 | 2.00 |
| 8 | 53 | female | Adenocarcinoma of the breast | 1.60 | |
| 9 | 77 | female | Adenocarcinoma of the lung | 1.92 | 2.00 |
| 10 | 78 | male | Adenocarcinoma of the prostate | 2.00 | |
| 11 | 69 | male | Adenocarcinoma of the prostate | 2.00 | |
| 12 | 46 | female | Adenocarcinoma of the breast | 2.00 | |
| 13 | 47 | female | Gastrointestinal stromal tumor | 2.00 | |
| 14 | 71 | male | Adenocarcinoma of the pancreas | 2.80 | 2.80 |
| 15 | 76 | male | Adenocarcinoma of the prostate | 2.80 | |

No deaths occurred. No patient withdrew from the study due to toxicity, and no Grade 3 or higher toxicity was seen. All observed toxicities are listed in Table 3.

TABLE 3

Toxicities developed during each treatment course (N = 20)

| Toxicity | Grade 1 | Grade 2 | Grade 3 | Grade 4 |
|---|---|---|---|---|
| Leukopenia | 5[1] | 1[2] | 0 | 0 |
| Anemia | 3 | 4[2] | 0 | 0 |
| Thrombocytopenia | 2 | 0 | 0 | 0 |
| Hypercalcemia | 8 | 0 | 0 | 0 |
| Creatinine elevation | 4 | 0 | 0 | 0 |
| Bilirubin elevation | 2 | 0 | 0 | 0 |
| ALT elevation | 1 | 0 | 0 | 0 |
| Alkaline phosphatase elevation | 2 | 1[2] | 0 | 0 |
| Nausea and vomiting | 5 | 2 | 0 | 0 |
| Diarrhea | 3 | 1 | 0 | 0 |
| Constipation | 5 | 0 | 0 | 0 |

TABLE 3-continued

Toxicities developed during each treatment course (N = 20)

| Toxicity | Grade 1 | Grade 2 | Grade 3 | Grade 4 |
|---|---|---|---|---|
| Dyspepsia | 4 | 0 | 0 | 0 |
| Headache | 5 | 0 | 0 | 0 |
| Fever | 2 | 0 | 0 | 0 |
| Skin rash | 1 | 0 | 0 | 0 |
| Bone or muscle pain | 8 | 0 | 0 | 0 |

[1] All were within normal limits of our laboratory (3.4–10.0 k/mm$^3$) but fell into the Grade 1 toxicity range of 3.0–3.9 k/mm$^3$
[2] All had Grade 1 abnormalities prior to entry onto study.

Figure 2:
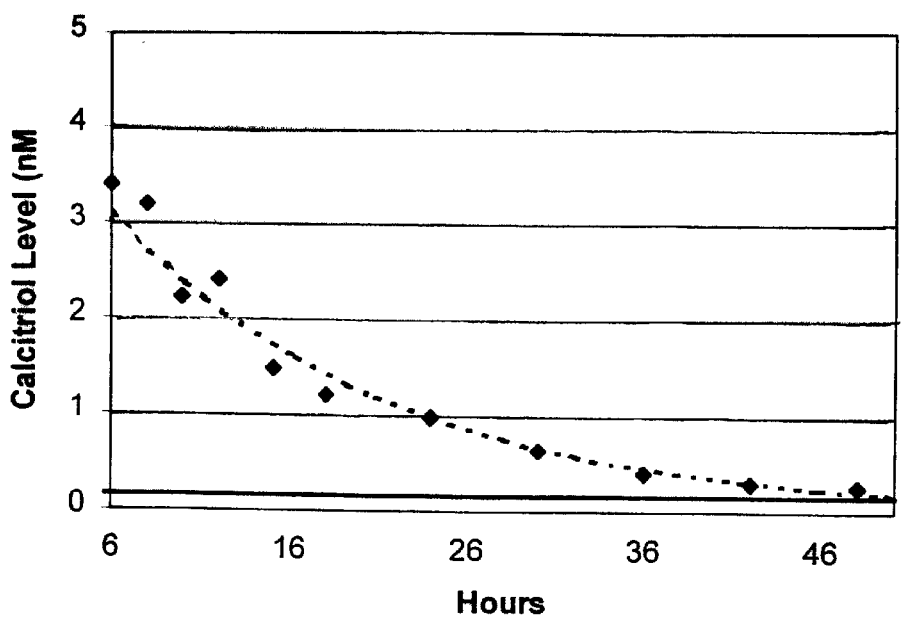
FIG. 2 shows a time course of plasma calcitriol levels in a subject who received a 2.0 µg/kg dose of calcitriol.

The normal range for serum 1,25-dihydroxyvitamin D levels is 0.05–0.16 nM(20–65 pg/ml). An approximately linear increase in the peak level was observed with increasing dose until the 0.48 µg/kg dose (Table 4, FIG. 1). Above this dose, a further elevation of peak levels was not seen. Serum 1,25-dihydroxyvitamin D trough levels returned to normal or near normal levels by 48 hours (FIG. 1). A limited study of calcitriol pharmacokinetics showed the expected decay in 1,25-dihydroxyvitamin D levels after hour 6 (FIG. 2).

TABLE 4

Mean Peak and 48 hour 1,25-dihydroxyvitamin D levels by dose

| Dose level (µg/kg) | Patients | Mean peak (nM) | Mean 48 hour level |
|---|---|---|---|
| 0.06 | 1 | 0.71 | 0.27 |
| 0.12 | 2 | 1.10 | 0.14 |
| 0.24 | 1 | 2.27 | 0.21 |
| 0.48 | 2 | 4.11 | 0.23 |
| 0.80 | 1 | 3.53 | |
| 0.96 | 1 | 3.83 | |
| 1.60 | 2 | 3.65 | |
| 1.92 | 1 | 3.34 | |
| 2.00 | 6 | 4.07 | 0.26 |
| 2.80 | 2 | 2.96 | |

Mean serum calcium (normal range 8.5–10.5 mg/dL) increased from 9.55 (SD 0.57) mg /dL prior to treatment to 9.76 (SD 0.63) mg/dL 24 hours later and to 9.88 (SD 0.68) mg/dL at 48 hours (p=0.0002 by a two way repeated measures analysis of variance). All calcium levels above the normal range returned to normal within 2 days with no intervention. Mean serum phosphate (normal range 2.2–4.2 mg/dL) increased from 3.43 (SD 0.56) mg/dL prior to treatment to 3.98 (SD 0.57) mg/dL 24 hours later and dropped to 3.86 (SD 0.53) mg/dL at 48 hours (p<0.0001 by a two way repeated measures analysis of variance). Mean 24 hour urinary calcium excretion (normal range 100–300 mg) increased from 130 (SD 62) mg with a range of 44–292 mg prior to treatment to 263 (SD 125) mg with a range of 59–594 on treatment, measured on day 2 of each treatment week (p<0.0001 by a one way repeated measures analysis of variance). There was no statistically significant increase in urinary calcium excretion during the treatment period by the Bonferroni/Dunn test.

Five of eight patients with measurable disease had stable disease. Among them, an adenocarcinoma of the lung patient, an adenocarcinoma of the pancreas patient, and a hepatocellular carcinoma patient received two cycles of therapy and remained stable for the entire 16 weeks of their time on study. The hepatocellular carcinoma patient had an associated 70% decline in her serum AFP level. The remaining three patients with measurable disease had evidence of progressive disease.

Four of seven patients without measurable disease had no evidence of progression. Among them was the breast cancer patient described in Example 3. A prostate cancer patient received two cycles of therapy, and had a stable PSA for the entire 16 weeks during which the drug was administered, in spite of a rapidly rising PSA prior to enrollment. The remaining three patients without measurable disease had either tumor marker or clinical evidence of progressive disease.

No patient developed dose-limiting hypercalcemic toxicity from calcitriol (<2 mcg/day). Measurements of peak blood calcitriol levels in patients indicate that blood levels (up to 8.9 nM) are at a level known to be growth inhibitory for cancer cells in culture. Furthermore, the drug calcitriol is essentially completely cleared from the blood by day 3, and this rapid clearance explains the increased safety profile of the weekly pulse schedule.

An unanticipated result was the finding that escalation of calcitriol dose beyond dose level 0.48 µg/kg did not result in further increases in peak calcitriol levels. More detailed measurement of calcitriol levels in one patient (dose level 2.0 µg/kg) indicated that absorption is saturated at high doses rather than delayed, as neither the peak levels of calcitriol are delayed and the half-life of the drug is not extended beyond the usual time observed in lower dose studies. The maximal tolerated dose (MTD) of calcitriol was not determined by the data presented in this example.

In summary, pulsed weekly administration of calcitriol allows substantial escalation of the total weekly dose of calcitriol that can be administered to patients with advanced malignancies. Peak blood levels of calcitriol about 25 fold above the upper limit of normal are achieved with minimal toxicity. These levels are well into the range where antiproliferative effects of calcitriol are observed. Based on the observation that blood levels of calcitriol do not increase linearly with increased dose beyond the 0.48 µg/kg level, a dose level of 0.5 µg/kg is an example of a dose that is therapeutically effective in patients whose tumor responds to this therapy, but which does not result in unacceptable hypercalcemia.

EXAMPLE 6

Preparation of Pharmaceutical Dosage Forms

Preparation of pharmaceutically acceptable compositions of the Vitamin D drugs of the present invention can be accomplished using methods well known to those with skill in the art. Any of the common carriers such as sterile saline solution, plasma, etc., can be utilized with the Vitamin D drugs of the invention. Routes of administration include but are not limited to oral, intracranial ventricular (icv), intrathecal (it), intravenous (iv), parenteral, rectal, topical ophthalmic, subconjunctival, nasal, aural and transdermal. The Vitamin D drugs of the invention may be administered intravenously in any conventional medium for intravenous injection such as an aqueous saline medium. Such medium may also contain conventional pharmaceutical adjunct materials such as, for example, pharmaceutically acceptable salts to adjust the osmotic pressure, buffers, preservatives and the like. Among such media are polysorbate, normal saline, lactated Ringer's solution, and plasma. Vitamin D is somewhat insoluble, hence solubilizng agents such as sesame oil, or equivalent lipophilic preparations, may be used to administer the Vitamin D drug.

Embodiments of the invention comprising medicaments, such as tablets or capsules, can be prepared with conventional pharmaceutically acceptable carriers, adjuvants and counterions as would be known to those of skill in the art. The medicaments are preferably in the form of a unit dose in solid, semi-solid and liquid dosage forms such as tablets, pills, powders, liquid solutions or suspensions, and injectable and infusible solutions, for example a unit dose vial. Effective dosage ranges included in the unit dose for calcitriol vary from about 5 mcg to about 100 mcg. The unit dosages of the clacitriol are much higher than previously used, because of the unanticipated finding that high pulse, therapeutically effective doses of the drug can be given without inducing symptomatic hypercalcemia.

EXAMPLE 7

Determining Binding Affinity

Binding affinity of the Vitamin D drugs for the Vitamin D receptor can be determined by any acceptable means, such as the VDR binding analysis and Scatchard plots in Peehl et al., *Cancer Research* 54:805–810, 1994., which is incorporated by reference.

VDR affinity can be assayed by a competitive receptor assay with radio-labeled calcitriol to determine the Relative Competitive Index (RCI) wherein the RCI for calcitriol is set at 100. The RCI of some of the Vitamin D analogs is set forth in Appendix 3.

EXAMPLE 8

Detecting Vitamin D Receptor on Tumor Cells

The presence of the VDR on tumor cells can be detected by the methods set forth in Peehl et al., which has been incorporated by reference in Example 7. A variety of other assays can be used to detect the VDR, including immunohistochemistry (Kaiser et al., *J. Cancer Res. Clin. Onc.* 122:356–359, 1996); Western blot (Cross et al., *Anticancer Research* 16:2333–2338, 1996); ligand binding assays and DNA probe hybridization to RNA (Northern blot) (*Endocrinology* 132:1952–1960); and detection of RNA by ribonuclease protection assay (Shabahang et al., *Annals of Surg. Onc.* 3:144–149, 1996).

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

The numerical values in the table for Relative Competitive Index (RCI) for the nuclear VDR and the RCI for the vitamin D binding protein (DBP) tabulate the data for the indicated parameter in relation to the result for $1\alpha,25(OH)_2D_3$ which is normalized to 100; thus the data values represent percentages of the $1\alpha,25(OH)_2D_3$ value. The key to the data entries is as follows. The RCI measures the relative ability of an analog under in vitro conditions to compete with $[^3H]1\alpha,25(OH)_2D_3$ for binding to the nuclear $1\alpha,25(OH)_2D_3$ receptor (VDR) (141) or the plasma vitamin D transport protein (DBP) (142). The cell differentiation data are related to that for $1\alpha,25(OH)_2D_3$ for which the value is set at 1.00. The calcemic index data are set at a value of 1.00 relative to that of $1\alpha,25(OH)_2D_3$.

SPC indicates the species of origin of the nVDR where c=chick intestine, r=rat intestine, b=bovine thymus, p=pig intestine, m=MCF-7 human breast cancer cells, z=rat osteosarcoma ROS 17/2.8 cells. For the DBP; all data are obtained from the human protein. The cell differentiation data are obtained in human transformed cell lines where h=HL-60 cells, u=U-937. The calcemic index is a measure of the relative ability of an analog to generate a "calcemic" response, which is defined differently depending upon the assay being conducted; c or i=a measure of intestinal $Ca^{2+}$ absorption (ICA) or bone $Ca^{2+}$ mobilizing activity (BCM) in the vitamin D-deficient chick (146,553); b=bone resorption; cbp=induction of the vitamin D-induced calcium binding protein, calbindin-$D_{28k}$; sc=elevation senrum $Ca^{2+}$= concentrations; oc=an increase in serum osteocalcin levels; r=an increase in urinary $Ca^{2+}$ excretion. Reference numbers are indicated in parentheses, and refer to regerence numbers in Boleillon et.al, 1995.

APPENDIX II
NCI Common Toxicity Criteria Used to Grade Toxicities

| Toxicity Grade | 0 | 1 | 2 | 3 | 4 |
|---|---|---|---|---|---|
| Blood/Bone Marrow | | | | | |
| WBC | >4.0K | 3.0–3.9K | 2.0–2.9K | 1.0–1.9K | <1K |
| Platelets | WNL | 75.0K–WNL | 50–74.9K | 25.0–49.9K | <25K |
| Hemoglobin | WNL | 10.0 g–WNL | 8.0–10.0 g | 6.5–7.9 g | <6.5 g |
| Neutrophils | >2.0K | 1.5–1.9K | 1.0–1.4K | 0.5–0.9K | <0.5K |
| Lymphocytes | >2.0K | 1.5–1.9K | 1.0–1.4K | 0.5–0.9K | <0.5K |
| Hemorrhage, Clinical | None | Mild, No Transfusions | Gross, 1–2 U PRBC | Gross, 3–4 U PRBC | Massive, >4 U PRBC |
| Infection | None | Mild | Moderate | Severe | Life-Threatening |
| Gastrointestinal | | | | | |
| Nausea | None | Able to Eat | Intake Decreased | No Significant Intake | |
| Vomiting | None | 1×/24 hours | 2–5×/24 hours | 6–10×/24 hrs | >10×/24 hrs |
| Diarrhea | None | Increase of 2–3×/24 hours | Increase of 4–6×/24 hours | Increase of 7–9×/24 hours | Increase of >10×/24 hrs |
| Stomatitis | None | Painless Ulcers | Painful Ulcers, Can Eat | Painful Ulcers, Cannot Eat | Requires IV Nutrition |

-continued

APPENDIX II
NCI Common Toxicity Criteria Used to Grade Toxicities

| Toxicity Grade | 0 | 1 | 2 | 3 | 4 |
|---|---|---|---|---|---|
| Hepatic | | | | | |
| Bilirubin | WNL | | <1.5× WNL | 1.5–3.0× WNL | >3× WNL |
| SGOT/SGPT | WNL | <2.5× WNL | 2.6–5.0× WNL | 5.1–20× WNL | >20× WNL |
| Alk Phos | WNL | <2.5× WNL | 2.6–5.0× WNL | 5.1–20× WNL | >20× WNL |
| Liver/Clinical | No Change | | | Precoma | Hepatic Coma |
| Kidney/Bladder | | | | | |
| Creatinine | WNL | <1.5× WNL | 1.5–3.0× WNL | 3.1–6.0× WNL | >6.0× WNL |
| Proteinuria | No Change | 1+ <0.3 gm % | 2–3+ 0.3–1.0 gm % | 4+ >1.0 gm % | Nephrotic Syndrome |
| Hematuria | Negative | Microscopic | Gross | With Clots | Transfusion |
| Alopecia | No Loss | Mild | Total | | |
| Cardiovascular | | | | | |
| Dysrhythmia | None | Asymptomatic No Therapy | Persistent No Therapy | Requires Therapy | Hypotension, V-tach/V-fib |
| Cardiac | None | Decline of EF by <20% | Decline of EF by >20% | Mild CHF, Rx Responsive | Refractory CHF |
| Ischemia | None | Nonspecific ST-T Wave changes | Asymptomatic Ischemic changes | Angina, No Infarction | Acute MI |
| Pericardial | None | Asymptomatic Effusion | Pericarditis, rub, EKG changes | Symptomatic Effusion | Tamponade |
| Hypertension | None | Transient, >20 mm Hg | Persistent, >20 mm, No Rx | Requires Therapy | Hypertensive Crisis |
| Hypotension | None | Transient, No Therapy | Fluid Replacement | Hospitalized <48 Hours | Hospitalized >48 Hours |
| Pulmonary | No Change | Asymptomatic Abnormal PFT | Dyspnea on Exertion | Dyspnea, no exertion | Dyspnea at Rest |

| Toxicity Grade | 0 | 1 | 2 | 3 | 4 |
|---|---|---|---|---|---|
| Neurologic | | | | | |
| Neuro-sensory | No Change | Mild Paresthesia | Moderate Sensory Loss | Severe Loss, Symptomatic | |
| Neuro-motor | No Change | Subjective Weakness | Mild Objective Weakness | Impairment of Function | Paralysis |
| Cortical | None | Mild Somnolence, Agitation | Moderate Somnolence, Agitation | Severe, with Contusion or Hallucination | Coma or Seizures |
| Cerebellar | None | Slight Change Coordination | Speech Slur Tremor, Nystagmus | Ataxia | Cerebellar Necrosis |
| Mood | No Change | Mild Anxiety or Depression | Moderate | Severe | Suicidal |
| Headache | None | Mild | Transient, Moderate–Severe | Unrelenting, Severe | |
| Constipation | None | Mild | Moderate | Severe | Ileus >96 Hrs |
| Hearing | No Change | Asymptomatic Audiometry changes | Tinnitus | Correctable Loss | Deaf, not Correctable |
| Vision | No Change | | | Symptomatic Subtotal Loss | Blindness |
| Skin | No Change | Macular/ Papular Rash, Asymptomatic | Rash with Pruritus | Generalized Eruption | Exfoliative or Ulcerative Rash |
| Allergy | None | Transient Rash, Temp <38□ C. | Urticaria, Mild Broncho-spasm, T>38□ C. | Serum Sickness, Bronchospasm | Anaphylaxis |
| Fever | None | 37.1–38□ C. | 38.1–40□ C. | >40□, <24 Hrs | >40□, >24 Hrs |
| Local | None | Pain | Inflammation Phlebitis | Ulceration | Plastic Surgery Rx |
| Weight Change | <5% | 5–9.9% | 10–19.9% | >20% | |
| Metabolic | | | | | |
| Hyper-Glycemia | <116 | 116–160 | 161–250 | 251–500 | >500, Ketoacidosis |
| Hypoglycemia | >64 | 55–64 | 40–54 | 30–39 | <30 |
| Amylase | WNL | <1.5× WNL | 1.5–2.0× WNL | 2.1–5.0× WNL | >5.1× WNL |
| Hyper-Calcemia | <10.6 | 10.6–11.5 | 11.6–12.5 | 12.6–13.5 | >13.5 |

APPENDIX II
NCI Common Toxicity Criteria Used to Grade Toxicities

| Toxicity Grade | 0 | 1 | 2 | 3 | 4 |
|---|---|---|---|---|---|
| Hypocalcemia | >8.4 | 8.4–7.8 | 7.7–7.0 | 6.9–6.1 | <6.0 |
| Hypo-Magnesemia | >1.4 | 1.4–1.2 | 1.1–0.9 | 0.8–0.6 | <0.5 |
| Coagulation | | | | | |
| Fibrinogen | WNL | .75–1× WNL | .5–.74× WNL | .25–.49× WNL | >24× WNL |
| PT | WNL | 1–1.25× WNL | 1.26–1.5× WNL | 1.51–2.0× WNL | >2.0× WNL |
| PTT | WNL | 1–1.25× WNL | 1.2–1.5× WNL | 1.51–2.0× WNL | >2.0× WNL |

APPENDIX III
Vitamin D Analogues

| Analogue | Manufacturer | Code Name | Relative Competitive index for VDR (Calcitriol = 100) | Dosing info | Comments |
|---|---|---|---|---|---|
| EB 1089 (24a,26a,27a,-Trihomo-22,24-diene-1a,25-(OH)$_2$—D$_3$) | Leo Pharmaceutical | IC | 17 (chick) | 0.1–0.5 mcg/kg qd | |
| KH 1060 (20-Epi-22-oxa-24a,26a,27a-trihomo-1,25-(OH)$_2$—D$_3$) | Leo Pharmaceutical | ID | 25 (chick) 120 (chick) | | CI = 1.3 |
| MC 1288 (1,25(OH$_2$-20-epi-D$_3$) | Leo Pharmaceuticals | IE | 147 (chick) 120 (chick) | | |
| MC 903 (Calcipotriol) (1,24S-(OH)$_2$-22-Ene-26,27-dehydro-D$_3$) | Leo Pharmaceutical | BT | 111 (chick) 240 (U-937 cells) 76 (chick) 100 (chick) | Rats - 50 mcg/kg qod | Topical form used in human breast cancer trial, approved as antipsoriatic CI < 0.01 |
| 1,25-(OH)2-16-Ene-D3 | Roche Pharmaceutical | HM | 165 (chick) 240 (rat intestine) 250 (rat intestine) | | |
| 1,25-(OH)2-16-Ene-23-yne-D$_3$ | Roche Pharmaceutical | V | 68 (chick) 70 (chick) 90 (chick) 50 (rat intestine) 80 (chick) | Mice - 0.5 mcg 3 ×/week, 1.6 mcg qod | |
| 25-(OH)2-16-Ene-23-yne-D$_3$ | Roche Pharmaceutical | AT | 0.4 (chick) <0.4 (chick) 0.07 (rat intestine) | | |
| 22-Oxacalcitriol (22-Oxa-1,25-(OH)$_2$-D$_3$) | Chugai Pharmaceutical | EU | 15 (chick) 12 (chick) 100 (rat osteosarcoma) 7 (chick) 100 (MCF-7 cells) | | CI < 0.001 |
| 1(OH)D$_5$ | University of Illinois | — | N/A | | |
| ZK 161422 (20-methyl-(1,25(OH)$_2$D3 | Institute of Medical Chemistry - Schering AG | — | N/A | | |
| ZK 157202 (20-methyl-23-ene(1,25(OH)$_2$D3 | Institute of Medical Chemistry - Schering AG | — | N/A | | |
| 1alpha-(OH)-D3 | | BP | 0.17 (chick) | | |

APPENDIX I

Summary of biological data for analogs of $1\alpha,25(OH)_2D_3$

| $1\alpha,25\text{-}(OH)_2\text{-VITAMIN } D_3 \text{ ANALOG NAME}$ | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| $1\alpha,25\text{-}(OH)_2\text{-}26,27\text{-}d_6\text{-}D_3$ | A | 0.85 100 | c r | (144) (227,186) | | | | | 1.00 | h | (186) | 0.92,0.64 | c | (227,186) |
| $1\alpha,25\text{-}(OH)_2\text{-}22\text{-ene-}D_3$ | B | 86 122 | c r | (144) (186) | 79 | (143) | 165 150 | (143) (143) | 1.25 | h | (186) | 0.9,1.3 | c,i | (186) |
| $1\alpha,25\text{-}(OH)_2\text{-}D_1$ | C | 100 | c | (144) | 100 | (143) | 100 | (143) | 1.00 | | | | | |
| $1\alpha,25\text{-}(OH)_2\text{-}26,27\text{-}F_6\text{-}22\text{-ene-}D_3$ | D | 21 60 | c r | (144) (186) | | | | | 30.00 | h | (186) | 2.2,1.1 | c,i | (186) |
| $1\alpha,25\text{-}(OH)_2\text{-}26,27\text{-}F_6\text{-}D_3$ | E | 15 90 30 <100 50 | c c c c r | (144) (220) (499,223) (226) (186) | 12 | (144) | 32 40 <100 40 | (143) (220) (499) (143) | 10.00 20.00 | h h | (223,558) (186) | 10 2.3,1.1 | sc c,i | (499) (186) |
| $1\alpha,25S\text{-}(OH)_2\text{-}26\text{-}F_3\text{-}D_3$ | F | 46 | c | (144) | 25 | (143) | | | | | | | | |
| $1\alpha,25\text{-}(OH)_2\text{-}24\text{-}F_2\text{-}D_3$ | G | 79 210 100 | c r c | (144) (186) (215,502) | 50 100 | (143) (211) | | | 7.00 20.00 2.00 10.00 | h h u h | (211) (212) (212) (186) | 1 10 10 4 2.35,0.6 >1 4 cbp 5 | c,i c sc sc c,i r (491,497) sc | (494) (214) (214) (209) (186) (215) (216) |
| $1\alpha,25S,26\text{-}(OH)_2\text{-}22\text{-ene-}D_3$ | H | 31 5 | c r | (144) (557) | 39 | (143) | 9 | (143) | 1.00 | h | (557) | | | |
| $1\alpha,25R,26\text{-}(OH)_2\text{-}22\text{-ene-}D_3$ | I | 29 | c | (144) | 50 | (143) | | | | | | | | |
| $1\alpha,25\text{-}(OH)_2\text{-}D_2$ | J | 61 100 100 | c c c,p,r | (144) (198,509,513) (550) | 64 | (143) | 370 | (143) | 0.50 | h | (193) | 1 1 | sc c,i | (513) (550) |
| $1\alpha,25\text{-}(OH)_2\text{-}24\text{-epi-}D_2$ | K | 21 50 30 20 | c r c c | (144) (509) (511,550) (198) | 22 | (144) | | | 1.00 | h | (246) | 0 0.5 0.3 | sc c,i c,i | (513) (246) (550) |
| $1\alpha,25\text{-}(OH)_2\text{-}23\text{-yne-}D_3$ | L | 71 40 | c r | (144) (186) | 74 | (143) | 25 23 | (143) (143) | 3.00 | h | (186) | 0.9,0.1 | c,i | (186) |
| $1\alpha,25\text{-}(OH)_2\text{-}24R\text{-}F\text{-}D_3$ | M | 87 140 115 | c c r | (144) (208) (186) | 151 | (143) | | | 0.30 | h | (186) | >1 0.6,0.4 | sc c,i | (209) (186) |

APPENDIX I (Continued)

| 1α,25-(OH)₂-VITAMIN D₃ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| 1α,25-(OH)₂-D₃-24,24,26,26,27-d₅ | N | 120 | c | (144) | | | 106 | (143) | 1.00 | h | (186) | 1.15 | c,i | (186) |
| | | 100 | c | (186) | | | 107 | (143) | | | | | | |
| 1α,25S,26-(OH)₃-D₃ | O | 88 | c | (144) | 92 | (143) | 4 | (143) | 0.14 | h | (186) | 0 | c | (186) |
| 1α,23S,25-(OH)₃-D₃ | P | 12 | c | (144) | | | 29 | (143) | 0.50 | h | (186) | 0.01 | c,i | (186) |
| 1α,23R,25-(OH)₃-D₃ | Q | 11 | c | (144) | | | | | | | | | | |
| | | 1 | r | (186) | | | | | | | | | | |
| 1α,24R-(OH)₂-25F-D₃ | R | 95 | c | (144) | 85 | (143) | | | | | | 1.002 | c,i | (559) |
| | | 0.2 | r | (186) | | | | | | | | | | |
| 1α,25-(OH)₂-26,27-F₆-23-yne-D₃ | S | 9 | c | (144) | | | | | | | | | | |
| 1α,25R-(OH)₂-26-F₃-D₃ | T | 70 | c | (144) | | | | | 3.00 | h | (186) | 2.16 | c,i | (186) |
| | | 190 | r | (186) | | | | | | | | | | |
| 1α,25,28-(OH)₃-D₂ | U | 9 | r | (144) | 63 | (143) | 22 | (143) | | | | <0.06 | c | (552) |
| 1α,25-(OH)₂-16-Ene-21-yne-D₃ | V | 68 | c | (144) | 76 | (143) | 9 | (143) | 10.00 | h | (186) | 0.03,0.02 | c,i | (349,188) |
| | | 70 | r | (188) | 75 | (189) | 10 | (189) | 2.00 | h | (349) | 0.03,0.02 | c,c | (189) |
| | | 90 | r | (127) | 79 | (188) | 5 | (143) | 5.00 | h | (189) | 0.5,0 | c,i | (187) |
| | | 50 | c | (186) | 60 | (349) | | | 10.00 | h | (187) | 0.05,0 | c,i | (186) |
| | | 90 | c | (349) | | | | | | | | | | |
| | | 80 | c | (189) | | | | | | | | | | |
| | | 50 | r | (187) | | | | | | | | | | |
| 1α,2-R,25-(OH)₂-D₃ | W | 39 | c | (144) | | | 21 | (143) | 0.20 | h | (186) | 0.9,0.2 | c,i | (186) |
| | | 2 | r | (186) | | | | | 0.25 | h | (193) | 1 | r | (533) |
| | | 39 | c | (190) | | | | | | | | | | |
| | | 15 | c | (144) | | | | | | | | | | |
| 1α,25-(OH)₂-26,27-F₆-23-enc-D₃ | X | 0.01 | c | (144) | | | 2500 | (143) | 0.01 | h | (186) | 0.10 | c,i | (186) |
| 25-(OH)-23-yne-D₃ | Y | <0.1 | r | (127) | | | 2970 | (143) | | | | | | |
| | | 0.06 | r | (186) | | | | | | | | | | |
| 25-(OH)₂-26,27-F₆-23-yne-D₃ | Z | 0.18 | r | (144) | | | 470 | (143) | | | | | | |
| 1α,25R-(OH)₂-22-Ene-26-F₆-D₃ | AB | 57 | c | (144) | | | | | | | | | | |
| 1α,25S-(OH)₂-22-Ene-26-F₆-D₃ | AC | 40 | c | (144) | | | | | | | | | | |

APPENDIX I (Continued)

| 1α,25-(OH)₂-VITAMIN D₃ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SP/C | (ref) | RCI | (ref) | RCI | (ref) | ED50 | (s) | (ref) | CI | (s) | (ref) |
| 1α,25R-(OH)₂-D₃-26,26,26-d₃ | AD | 90 | c | (144) | | | | | | | | 1.4 | c,i | (227) |
| | | 83 | r | (227) | | | | | | | | | | |
| 1α,25S-(OH)₂-D₃-26,26,26-d₃ | AE | 129 | c | (144) | | | | | | | | 0.9,1.5 | c,i | (227) |
| | | 150 | r | (227) | | | | | | | | | | |
| 1α,25R-(OH)₂-22-Ene-D₃-26,26,26-d₁ | AF | 133 | c | (144) | | | | | | | | | | |
| 1α,25S-(OH)₂-22-Ene-D₃-26,26,26-d₁ | AG | 125 | c | (144) | | | | | | | | | | |
| 1α,25-(OH)₂-D₃-26,26,26,27,27,27-d₆ | AH | 11 | r | (144) | | | | | | | | | | |
| 1α,25-(OH)₂-24-Epi-D₃-26,26,26,27,27,27-d₆ | AI | | | | | | | | | | | | | |
| 1α,25-(OH)₂-D₃-23,23,24,24,26,26,26,27,27,27-d₁₀ | AJ | | | | | | | | | | | | | |
| 1α,25-(OH)₂-22-Ene-D₃-26,26,26,27,27,27-d₆ | AK | | | | | | | | | | | | | |
| 9(11)-Dehydro-3-deoxy-1,25-(OH)₂-D₃ | AM | 5 | c | (144,61) | | | | | | | | | | |
| 2-Nor-1,3-seco-1,25-(OH)₂-D₃ | AN | 3 | c | (144) | | | | | | | | | | |
| 2,4-Dinor-1,3-seco-1,25-(OH)₂-D₃ | AP | 2 | c | (144) | | | | | | | | | | |
| 1,1-Dimethyl-2,4-dinor-1,3-seco-1,25-(OH)₂-D₃ | AQ | 0.11 | c | (144) | | | | | | | | | | |
| 3-Deoxy-2-oxa-25-(OH)-D₃ | AR | 11 | c | (144) | | | | | | | | | | |
| 24R,25-(OH)₂-D₃ | AS | 0.03 | c | (144) | | | 33800 | (143) | <0.01 | u | (196) | <0.01 | uc | (196) |
| | | 0.1 | c | (196) | | | | | 0.02 | h | (481) | 0 | sc | (482,483) |
| | | | | | | | | | >0.01 | h | (193) | 0.1 | i | (532) |
| 25-(OH)-16-Ene-23-yne-D₃ | AT | 0.4 | c | (144) | 16 | (143) | 130 | (143) | 0.01 | h | (186) | 0.7,0 | c,i | (186) |
| | | <0.4 | c | (127) | | | 101 | (143) | 0.05 | h | (187) | 0.02, | i,c | (189) |
| | | 0.07 | r | (186) | | | | | | | | 0.001 | | |
| | | 0.4 | c | (189) | | | | | | | | 0.7,0 | c,i | (187) |
| | | 0.07 | r | (187) | | | | | | | | | | |
| 1-F-25-(OH)-16-Ene-23-yne-D₃ | AU | 21 | c | (144) | 36 | (143, 189) | | | 4.00 | h | (189) | 0.0003, | c,i | (189) |
| | | | | | | | | | | | | 0.0008 | | |
| 1α,25-(OH)₂-16-Ene-23-yne-D₃-26,26,26,27,27,27-d₆ | AV | 110 | c | (144) | 46 | (143) | | | 3.00 | h | (189) | 0.01, | i,c | (189) |
| | | | | | | | | | | | | 0.004 | | |
| 1-F-25-(OH)-16-ene-23-yne-D₃-26,26,26,27,27,27-d₆ | AW | 98 | c | (189) | 46 | (189) | | | 1.00 | h | (189) | 0.0002, | c,i | (189) |
| | | 16 | r | (189) | 55 | (143,189) | | | | | | 0.002 | | |

APPENDIX I (Continued)

| 1α,25-(OH)₂-VITAMIN D₃ ANALOG NAME | ANA-LOG | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | CODE NAME | RCI | SPC | (ref) | RCI | (ref) | RCI | (ref) | ED50 | (s) | (ref) | CI | (s) | (ref) |
| A-Homo-3-deoxy-3,3-dimethyl-1,2,4-dioxa-25-(OH)₂-D₃ | AX | 4 | c | (144) | | | | | | | | | | |
| 24-Nor-1α,25-(OH)₂-D₃ | BA | 67 | c | (144) | | | 20 | (143) | 0.07 | h | (247) | 0.02 | c,i | (188) |
| | | 1 | c | (188) | | | | | 0.076 | h | (193) | | | |
| 25-Oxo-25-phospha-D₃ | BB | 11 | c | (144) | | | | | | | | | | |
| 9(11)Dehydro-11-(4-hydroxymethylphenyl)-1,25(OH)₂-D₃ | BD | 3 | c | (144) | 0.75 | (143) | | | | | | | | |
| (23S,25S)-1α,25-(OH)₂-D₃-26,23-lactone | BF | 12 | c | (144) | | | | | | | | 0.3 | sc | (336) |
| | | 8 | c | (535,536) | | | | | | | | 0.25 | c | (336) |
| 1α,11β,25-(OH)₃-D₃ | BG | 5 | c | (144) | | | 7 | (143) | | | | | | |
| 9(11)Dehydro-11(3'-hydroxypropyn-1'-yl)-1,25-(OH)₂-D₃ | BH | 3 | c | (144) | | | | | | | | | | |
| 9(11)Dehydro-11(3'-acetoxypropyn-1'-yl)-1,25-(OH)₂-D₃ | BI | 0.7 | c | (144) | 1 | (143) | | | | | | | | |
| 9(11)Dehydro-11(4-acetoxymethylphenyl)-1,25-(OH)₂-D₃ | BJ | 1 | c | (144) | | | | | | | | | | |
| Vitamin-D₃ | BN | 0.0001 | c | (144) | | | 2298 | (143) | | | | | | |
| 25-(OH)-D₃ | BO | 0.15 | c | (144) | | | 66700 | (143) | | | | | | |
| 1α-(OH)-D₃ | BP | 0.17 | c | (144) | 0.005 | (143) | 62 | (143) | | | | 0.02 | c | (336) |
| (23S,25S)-1α,25-(OH)₂-D₃-26,23-lactone | BQ | 0.3 | c | (143) | | | | | | | | 0.0 | sc | (336) |
| | | 3 | c | (501) | | | | | | | | | | |
| | | 0.2 | c | (535,536) | | | | | | | | | | |
| (23R,25R)-1α,25-(OH)₂-D₃-26,23-lactone | BR | 1 | c | (144) | | | | | | | | 0.1 | c | (536) |
| | | 2 | c | (535,536) | | | | | | | | 0.0 | sc | (536) |
| (23S,25R)-1α,25-(OH)₂-D₃-26,23-lactone [Natural Form] | BS | 0.5 | c | (144) | 0.5 | (211) | 280 | (501) | 0.004 | h | (211) | <0.01 | sc | (195) |
| | | 1 | c | (501) | | | | | | | | 0.01 | c | (533) |
| | | 0.1 | c | (533) | | | | | | | | 0.013 | c | (536) |
| | | 0.2 | c | (535,536) | | | | | | | | 0 | sc | (536) |
| 1α,24S-(OH)₂-22-Ene-26,27-dehydro-D₃ | BT | 111 | c | (144) | 131 | (143) | 49 | (143) | 1.00 | a | (543) | <0.01 | | (543) |
| | | 240 | n | (530) | | | 70 | (461) | 1.00 | a | (530) | <0.01 | sc | (530) |
| | | 76 | c | (322) | | | 55 | (143) | 1.00 | a | (127) | <0.01 | sc | (127) |
| | | 100 | c | (127) | | | | | 1.00 | a | (196) | <0.005 | sc | (461) |
| | | 100 | c | (530) | | | | | 1.00 | a | (530) | 0.05 | sc | (196) |
| | | 100 | c | (196) | | | | | 1.00 | h | (162) | | | (530) |
| 9(11)-Dehydro-1α,25-(OH)₂-D₃ | BU | 35 | c | (144) | | | 116 | (143) | | | | | | |
| | | 30 | c | (61) | | | 66 | (143) | | | | | | |
| 1α,11α,25-(OH)₃-D₃ | BW | 2 | c | (144) | | | 20 | (143) | | | | | | |
| 11β-Methoxy-1α,25-(OH)₂-D₃ | BX | 40 | c | (144) | 138 | (143) | 24 | (143) | | | | | | |

-22-

APPENDIX I (Continued)

| 1α,25-(OH)₂-VITAMIN D₃ ANALOG NAME | ANA-LOG | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | CODE NAME | RCI | SPC | (ref) | RCI | (ref) | RCI | (ref) | ED50 | (s) | (ref) | CI | (s) | (ref) |
| 11α-Methoxy-1α,25-(OH)₂-D₃ | BY | 5 | c | (144) | 96 | (143) | | | | | | | | |
| 25-(OH)₂-23-Oxa-D₃ | BZ | 6 | c | (144) | | | | | | | | | | |
| 1α,24S,25-(OH)₃-D₃ | CA | 4 | c | (190) | | | | | | | | | | |
| 3-Deoxy-1α,25-(OH)₂-D₃ | CF | 6 | c | (144) | | | | | | | | 0.2, <0.1 | c,i | (538) |
| | | 3 | c | (61) | | | | | | | | 1 | c | (531) |
| | | 6 | c | (538) | | | | | | | | | | |
| | | 13 | c | (531) | | | | | | | | | | |
| 1α,24R-(OH)₂-D₃ | CT | 94 | c | (144) | 66 | (143) | | | 0.01 | u | (196) | 1 | u | (196) |
| | | 100 | c | (190,196) | | | | | 1.00 | h | (193) | 1 | c,i | (197) |
| 1α,24S-(OH)₂-D₃ | CU | 9 | c | (144) | | | | | 1.00 | h | (503) | 1 | c,i | (197) |
| | | 10 | c | (190) | | | | | 0.50 | h | (193) | | | |
| 1α,25-(OH)₂-24-Oxo-D₃ | CW | 98 | c | (144) | | | | | | | | | | |
| 1α,21,25-(OH)₃-24-Oxo-D₃ | CX | 28 | c | (144) | | | | | | | | 0.003, c,i | | (188) |
| 1α-(OH)-25-Oxo-25-phospha-D₃ | DA | 0.4 | c | (188) | | | | | | | | 0.001 | | |
| | | 0.3 | c | (144) | | | | | | | | | | |
| 25-Oxo-26,27-dimethyl-25-phospha-26,27-dioxa-D₃ | DB | 0.02 | c | (144) | | | | | | | | 0.002, c,i | | (188) |
| 1α-(OH)-25-oxo-26,27-dimethyl-25-phospha-26,27-dioxa-D₃ | DC | 7 | c | (144) | | | 3 | (143) | 0.00 | h | (537) | 0.001 | | (537) |
| | | 7 | c | (188,537) | | | | | | | | 0.02, c,i | | |
| | | | | | | | | | | | | 0.001 | | |
| 22-(Meta-hydroxyphenyl)-1α,25-(OH)₂-D₃ | DE | 29 | c | (144) | 26 | (143) | 980 | (143) | | | | | | |
| 22-(Para-hydroxyphenyl)-1α,25(OH)₂-D₃ | DF | 5 | c | (144) | 8 | (143) | 1980 | (143) | | | | 0.06, c,i | | (179) |
| 1α,25-(OH)₂-5,6-trans-D₃ | DI | 13 | c | (179) | | | | | | | | 0.015 | | |
| 25R,26-(OH)₂-D₃ | DJ | | | | | | | | | | | <0.1 sc | | (561) |
| 25S,26-(OH)₂-D₃ | DK | | | | | | 26792 | (143) | | | | | | |
| 1α,25S,26-(OH)₃-D₃ | DM | | | | | | 42 | (143) | | | | | | |
| 1α,15R,26-(OH)₃-D₃ | DN | 80 | c | (127) | | | | | | | | 0.25 sc | | (195) |
| (23R,25S)-25-OH-D₃-26,23-lactone | EC | 0.04 | c | (501) | | | 14100 | (501) | | | | | | |

APPENDIX I (Continued)

| 1α,25-(OH)₂-VITAMIN D₃ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| (23S,25R)-25-OH-D₃-26,23-lactone | ED | 0.0001 | c | (501) | | | 14100 | (501) | | | | | | |
| 6-Fluoro-D₃ | EM | 0.001 | c | (144) | | | | | | | | 0 | c | (500,554) |
| | | 0.3 | c | (500) | | | | | | | | | | |
| 1α,25-(OH)₂-16-Ene-23-yne-26,27-F₆-D₃ | EO | 46 | c | (144) | 31 | (143,188) | 15 | (143) | 80.00 | h | (188,189) | 0.06 | c,i | (188) |
| | | 45 | c | (188) | | | 25 | (143) | | | | | | |
| 25-(OH)-16-Ene-23-yne-26,27-F₆-D₃ | EP | 0.6 | c | (143) | | | 10 | (143) | | | | 0.001 | c,i | (188) |
| | | 0.6 | c | (188) | | | | | | | | 0.02 | | |
| 1α-F-25-(OH)₂-16-ene-23-yne-26,27-F₆-D₃ | EQ | 20 | c | (144) | 9 | (143,188) | 72 | (143) | 1.00 | h | (189) | 0.005 | c,i | (188) |
| | | 5 | | (188) | | | 105 | (143) | 5.70 | h | (188) | 0.002 | | |
| 1α,25-(OH)₂-24a-Homo-D₃ | ER | 55 | c | (144) | 54 | (143) | 8 | (143) | 10.00 | h | (249,250) | 0.2 | i,c | (249) |
| | | 100 | r | (249) | 100 | (249) | | | 10.00 | h | (247) | <0.1 | i,c | (250) |
| | | 100 | c | (247) | | | | | 7.6 | h | (193) | | | |
| 1α,25-(OH)₂-24a-Dihomo-D₃ | ES | 25 | c | (144) | 16 | (143) | 8 | (143) | 10.00 | h | (250) | <0.01 | c,i | (250) |
| | | 3 | r | (250) | 3 | (250) | | | | | | | | |
| 22(m-methylphenyl)-23,24,25,26,27-pentanor-1α-(OH)-D₃ | ET | 1 | r | (144) | 4 | | | | | | | | | |
| 22-Oxa-1α,25-(OH)₂-D₃ | EU | 15 | c | (144) | 53 | | 23 | (143) | 10.00 | h | (510) | 0.01 | sc | (231) |
| | | 12 | c | (233) | 10 | (231-233) | 0.2 | (233) | 0.00 | | | | | |
| | | 100 | r | (235) | | | <0.1 | (231) | 10.00 | h | (236) | 0.004 | u | (238) |
| | | 10 | | (232) | | | <0.2 | (232) | 10.00 | h | (556) | <0.001 | sc | (156) |
| | | 7 | | (510) | | | 22 | (143) | | | | <0.01 | i,sc | (237) |
| | | 100 | m | (231) | | | <0.20 | (291) | | | | | | |
| 22(m-(dimethylhydroxymethyl)phenyl)-23,24,25,26,27-pentanor-1α-(OH)-D₃ | EV | 62 | c | (144) | 59 | (143) | 13.4 | (143) | | | | | | |
| | | | | | | | 25 | (143) | | | | | | |
| 1α,25-(OH)₂-22-Ene-D₃ | EX | 86 | c | (144) | | | 40 | (143) | | | | | | |
| 25-(OH)₂-23-Ene-D₃ | EY | | | | | | 24498 | (143) | 0.01 | h | (191) | | | |
| 1α,25-(OH)₂-16,23(E)-diene-D₃ | EZ | 80 | r | (186,187) | | | 17 | (143) | 3.00 | h | (186,187) | 1.4,0.8 | c,i | (187) |
| 1-Epi-1α,25-(OH)₂-D₃ | GE | 15 | c | (144) | | | 12 | (143) | | | | | | |
| 1-Epi-1α,25-(OH)₂-pre-D₃ | GF | 2 | c | (144) | | | 2 | (143) | | | | | | |
| 3-Deoxy-3-thia-1α,25-(OH)₂-D₃ | HA | 15 | c | (518) | | | | | | | | 0.2,<0.1 | c,i | (538) |
| 3-Deoxy-3-thia-1β,25-(OH)₂-D₃ | HB | 1 | c | (538) | | | | | | | | <0.2,<0.1 | c,i | (538) |
| 1α,25-(OH)₂-pre-D₃-9,14,19,19-d₄ | HF | 10 | c | (92) | | | 9 | (143) | <0.05 | h | (92) | <0.05 | sc | (92) |
| | | | | | | | 7 | (92) | | | | | | |
| 1α,25-(OH)₂-D₃-9,9,14,19,19-d₅ | HG | 90 | c | (144) | | | 51 | (143) | 0.90 | h | (92) | >1 | sc | (92) |

APPENDIX I (Continued)

| 1α,25-(OH)$_2$-VITAMIN D$_3$ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| | | 92 | c | (92) | | | 60 | (143) | | | | | | |
| | | | | | | | 95 | (92) | | | | | | |
| 1α,25-(OH)$_2$-23-epi-D$_3$ | HH | 0.22 | c | (144) | | | 6570 | (143) | | | | | | |
| 1α,25-(OH)$_2$-6,7-Dehydro-pre-D$_3$ | HI | 3 | c | (144) | | | | | | | | | | |
| 1α,25-(OH)$_2$-3-epi-D$_3$ | HJ | 24 | c | (144) | | | 800 | (143) | | | | | | |
| 1β,25-(OH)$_2$-6,7-Dehydro-3-epi-pre-D$_3$ | HK | 0.05 | c | (144) | | | | | | | | | | |
| 1β,25-(OH)$_2$-D$_3$ | HL | 0.00 | c | (144) | | | 449 | (143) | | | | <0.001 | i,c | (496) |
| | | <0.8 | r | (132) | | | | | | | | | | |
| | | <0.1 | | (506) | | | | | | | | | | |
| 1α,25-(OH)$_2$-16-Ene-D$_3$ | HM | 165 | c | (144) | 150 | (143) | 2 | (143) | 5.00 | h | (186,187) | 0,0.6 | c,i | (187) |
| | | 240 | r | (186,187) | | | | | | | | 0 | | (171) |
| | | 250 | r | (171) | | | | | | | | | | |
| 25-(OH)-16-Ene-D$_3$ | HN | 0.7 | c | (144) | 0.06 | (143) | 489 | (143) | 0.03 | h | (186) | 1,0 | c,i | (187) |
| | | 0.01 | c | (127) | 0.03 | (143) | 233 | (143) | 0.01 | h | (187) | | | |
| | | 0.2 | r | (186) | | | | | | | | | | |
| | | 0.2 | r | (187) | | | | | | | | | | |
| 25-(OH)-16,23-Diene-D$_3$ | HO | 0.1 | r | (186) | | | 524 | (143) | 0.005 | h | (186) | 2.5,0 | c,i | (187) |
| | | 0.1 | r | (187) | | | | | 0.02 | h | (187) | 2.5 | c | (171) |
| | | 0.1 | r | (171) | | | | | | | | | | |
| 1α,2,25-(OH)$_3$-D$_3$ | HP | 70 | c | (144) | | | | | | | | | | |
| (22S)-1α,25-(OH)$_2$-22,23-Diene-D$_3$ | HQ | 21 | c | (144) | | | 25 | (143) | | | | | | |
| (22R)-1α,25-(OH)$_2$-22,23-Diene-D$_3$ | HR | 52 | c | (144) | | | 48 | (143) | | | | | | |
| | | | | | | | 47 | (143) | | | | | | |
| 1α,18,25-(OH)$_3$-D$_3$ | HS | 25 | c | (144) | | | | | 0.50 | h | (184) | <1 | c | (184) |
| | | 20 | b | (184) | | | | | | | | | | |
| 1α,18-(OH)$_2$-D$_3$ | HV | 0.02 | c | (144) | | | | | | | | | | |
| 18-Acctoxy-1α,25-(OH)$_2$-D$_3$ | HW | 0.04 | c | (144,183) | | | | | | | | 0.001 | c,i | (183) |
| | | | | | | | | | | | | 0.01 | | |
| 18-Acetoxy-1α-(OH)-D$_3$ | HZ | 0.02 | c | (144,183) | | | | | | | | <0.0005 | c | (183) |
| | | | | | | | | | | | | <0.001 | c | (183) |
| 23-(m-(Dimethylhydroxymethyl)phenyl)-22-yne-24,25,26,27-tetranor-1α-(OH)-D$_3$ | IB | 1 | c | (144) | | | | | | | | | | |

APPENDIX I (Continued)

| 1α,25-(OH)₂-VITAMIN D₃ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | | |
|---|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) | |
| 24,26,27a,-Trihomo-22,24-diene-1α,25-(OH)₂-D₃ | 1C | 17 | c | (144) | | | | | | | | | | | |
| 20-Epi-22-oxa-24a,26a,27a-trihomo-1α,25-(OH)₂-D₃ | 1D | 25 | c | (144) | | | | | 20000 | u | (244) | 1.3 | r | (244,160) | |
| | | 120 | c | (244) | | | | | | | | | | | |
| 20-Epi-1α,25-(OH)₂-D₃ | 1E | 117 | c | (144) | | | | | 27.00 | u | (244) | 2.3 | u | (244,160) | |
| | | 120 | c | (244) | | | | | | | | | | | |
| 20-Epi-24a,26a,27a-trihomo-1α,25-(OH)₂-D₃ | 1F | 23 | c | (144) | | | | | 200.0 | u | (244) | 1.2 | r | (244,160) | |
| | | 100 | c | (244) | | | | | | | | | | | |
| 18-oxo-1α,25-(OH)₂-D₃ | 1G | 26 | c | (144) | | | | | | | | | | | |
| 3-Deoxy-3-thia-1α,25-(OH)₂-D₃-3β-oxide | 1I | 27 | c | (144) | | | | | | | | | | | |
| 5,6-trans-3-Deoxy-3-thia-1α,25-(OH)₂-D₃-3β-oxide | 1K | 4 | c | (144) | | | | | | | | | | | |
| 24a-Homo-22,24(24a)-diene-1α,25-(OH)₂-D₃ | 1P | 26 | c | (144) | | | | | | | | | | | |
| 24a-Dihomo-1α,22R,25-(OH)₃-D₃ | 1Q | 2 | c | (144) | | | | | | | | | | | |
| 8,(14a)-homo-1α,25-(OH)₂-D₃ | KB | | | | | | 20 | (182) | 1.00 | h | (182) | 0.1 | sc | (182) |
| 21-oxa-1α,25-(OH)₂-D₃ | KD | | | | | | | | 0.20 | h | (242) | | | | |
| | | | | | | | | | <.001 | h | (563) | | | | |
| 1α-(hydroxymethyl)-25-OH-D₃ | ZAA | <0.1 | c | (173) | | | | | | | | <0.001 | c | (173) | |
| 1β-(hydroxymethyl)-3α,25-(OH)₂-D₃ | ZAB | <0.1 | c | (173) | | | | | | | | <0.001 | c | (173) | |
| 2β-(3-hydroxypropoxy)-1α,25-(OH)₂-D₃ | ZAC | 10 | c | (222) | | | 200 | (222) | | | | 1.1c | | (516) | |
| | | 12 | c | (516) | | | 200 | (516) | | | | | | | |
| 1α,25-(OH)₂-24(S)-5,6-t-D₃ | ZAD | 50 | c | (198) | | | | | | | | | | | |
| 1α,25-(OH)₂-24(R)-5,6-t-D₃ | ZAE | 1 | c | (198) | | | | | | | | | | | |
| 11α-phenyl-1α,25-(OH)₂-D₃ | ZAF | <1 | r | (140) | | | 200 | (140) | 0.03 | h | (140) | <0.01 | c | (140) | |
| 11β-phenyl-1α,25-(OH)₂-D₃ | ZAG | 5 | r | (140) | | | 150 | (140) | 0.07 | h | (140) | <0.01 | c | (140) | |
| 11α-dimethylaminophenyl-1α,25-(OH)₂-D₃ | ZAH | 1 | r | (140) | | | 1 | (140) | <.001 | h | (140) | <0.01 | c | (140) | |
| 11α-methyl-1α,25-(OH)₂-D₃ | ZAI | 230 | r | (140) | | | 140 | (140) | 1.13 | h | (140) | 0.4 | c | (140) | |
| 11β-methyl-1α,25-(OH)₂-D₃ | ZAJ | 37 | r | (140) | | | 86 | (140) | 0.19 | h | (140) | 0.02 | c | (140) | |
| 11α-hydroxymethyl-1α,25-(OH)₂-D₃ | ZAK | <1 | r | (140) | | | 107 | (140) | 0.07 | h | (140) | <0.01 | c | (140) | |
| 11α-fluoromethyl-1α,25-(OH)₂-D₃ | ZAL | 75 | r | (140) | | | 250 | (140) | 0.63 | h | (140) | 0.1 | c | (140) | |
| 11α-chloromethyl-1α,25-(OH)₂-D₃ | ZAM | 12 | r | (140) | | | 160 | (140) | 0.28 | h | (140) | 0.1 | c | (140) | |
| 11α-ethyl-1α,25-(OH)₂-D₃ | ZAN | 9 | r | (140) | | | 272 | (140) | 0.43 | h | (140) | 0.02 | c | (140) | |
| 11α-(2-hydroxyethyl)-1α,25-(OH)₂-D₃ | ZAO | 0.1 | r | (140) | | | 115 | (140) | 0.07 | h | (140) | <0.01 | c | (140) | |
| 11β-(2-hydroxyethyl)-1α,25-(OH)₂-D₃ | ZAP | <1 | r | (140) | | | 40 | (140) | 0.05 | h | (140) | <0.01 | c | (140) | |
| 11α-vinyl-1α,25-(OH)₂-D₃ | ZAQ | 21 | r | (140) | | | 380 | (140) | 0.81 | h | (140) | <0.01 | c | (140) | |

WO 99/49870 PCT/US99/06442

APPENDIX I (Continued)

| 1α,25-(OH)₂-VITAMIN D₃ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| — 1α,25-(OH)₂-VITAMIN D₃ | | | | | | | | | 2.26 | h | (140) | 0.16 | c | (140) |
| 11α-ethynyl-1α,25-(OH)₂-D₃ | ZAR | 210 | r | (140) | | | 25 | (140) | <0.01 | h | (140) | | | |
| 11α-[1'(R)-oxacyclopropyl]-1α,25-(OH)₂-D₃ | ZAS | 2 | r | (140) | | | 80 | (140) | <0.01 | h | (140) | | | |
| 11α-[1'(S)-oxacyclopropyl]-1α,25-(OH)₂-D₃ | ZAT | 1 | c | (140) | | | 62 | (140) | <0.01 | h | (140) | | | |
| 1α,25-(OH)₂-13-vinyl-18-nor-D₃ | ZAU | 25 | b | (184) | | | 100 | (184) | 0.50 | h | (184) | <1 | c | (184) |
| 25-(OH)₂-16,23(Z)-diene-D₃ | ZAW | 0.8 | r | (187) | | | | | <0.01 | h | (187) | | | |
| 1α,25-(OH)₂-16,23(Z)-diene-D₃ | ZAX | 145 | r | (187) | | | 17 | (187) | 1.00 | h | (187) | | | |
| 1α,25-(OH)₂-18-methyl-D₃ | ZAY | 100 | b | (184) | | | 100 | (184) | 0.50 | h | (184) | <1 | c | (184) |
| 1α,25-(OH)₂-19-nor-pre-D₃ | ZAZ | 1 | p | (176) | | | 6 | (176) | 0.01 | h | (176) | 0 | sc | (176) |
| 1α,25-(OH)₂-19-nor-D₃ | ZBA | 20 | p | (176) | | | 20 | (176) | 1.00 | h | (176) | <0.1 | sc | (176) |
| 25,26-epoxy-23-yne-19-nor-1α-(OH)-D₃ | ZBB | 20 | p | (204) | | | 1 | (204) | 0.12 | h | (204) | <0.01 | c | (204) |
| 20-epi-24-homo-1α,25-(OH)₂-D₃ | ZBC | 110 | c | (244) | | | | | 200.0 | c | (244) | 5 | r | (244,160) |
| 20-epi-22-oxa-1α,25-(OH)₂-D₃ | ZBD | 2 | c | (244) | | | | | 4.00 | c | (244) | 0.1 | r | (244) |
| 20-epi-22-oxa-24-homo-1α,25-(OH)₂-D₃ | ZBE | 3 | c | (244) | | | | | 1176 | u | (244) | 3 | r | (244) |
| 20-epi-22-oxa-24-dihomo-1α,25-(OH)₂-D₃ | ZBF | 35 | c | (244) | | | | | 400.0 | u | (244) | 1.4 | r | (244) |
| 20-epi-22-oxa-24-dihomo-26,27-dihomo-1α,25-(OH)₂-D₃ | ZBG | 60 | c | (244) | | | | | 400.0 | u | (244) | 0.8 | r | (244) |
| 20-epi-22-oxa-24a,24b-dihomo-1α,25-(OH)₂-D₃ | ZBH | 60 | c | (548) | | | | | 1000 | u | (548) | 0.6 | u | (548) |
| 25,26-epoxy-23-yne-20-epi-1α-(OH)₂-D₃ | ZBI | 102 | p | (204) | | | 0 | (204) | 20.00 | h | (204) | 0.03 | c | (204) |
| 1α-(OH)-20-oxa-21-nor-D₃ | ZBJ | 0.1 | c | (240) | | | | | 1.00 | h | (240) | | | |
| | | | | | | | | | 0.20 | h | (510) | | | |
| | | | | | | | | | <0.05 | h | (236) | | | |
| 1α,25-(OH)₂-20-oxa-21-nor-D₃ | ZBK | 0.1 | c | (240) | | | | | 1.00 | h | (240) | 0 | i,c | (240) |
| | | | | | | | | | 0.20 | h | (556,510) | | | |
| | | | | | | | | | 0.1 | h | (236) | | | |
| 22-oxa-1α-(OH)-D₃ | ZBL | 1 | c | (510) | | | | | <0.10 | h | (236) | | | |
| 1α,24(S)-(OH)₂-22-oxa-D₃ | ZBM | | | | | | | | 10.00 | h | (239) | | | |
| 1α,24(S)-(OH)₂-22-oxa-26,27-dimethyl-D₃ | ZBN | | | | | | | | 10.00 | h | (239) | | | |
| 1α,25-(OH)₂-22-oxa-26,27-dimethyl-D₃ | ZBO | | | | | | | | 10.00 | h | (239) | | | |
| 22-(OH)₂ | ZBP | <0.1 | c | (505) | | | 500 | (505) | 0.01 | h | (191) | <0.001 | cbp | (505) |
| 1α-(OH)-22-oxo-D₃ | ZBQ | | | | | | | | 0.005 | h | (193) | | | |
| 23,24,25,26,27-pentanor-1,22-(OH)₂-D₃ | ZBR | | | | | | | | | | | | | |

-27-

APPENDIX I (Continued)

| 1α,25-(OH)₂-VITAMIN D₃ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| 1α,25-(OH)₂-22-E-ene-D₃ | ZBS | 0.1 | c | (504) | | | | | 0.02 | h | (193) | | | |
| 1α,(OH)₂-22-Z-ene-D₃ | ZBT | | | | | | | | <0.01 | h | (193) | | | |
| 1α,25(OH)₂-22-ene-24-homo-D₃ | ZBU | 100 | r | (249) | | | | | 10.00 | h | (249, 247) | 1,<0.2 | ci | (249) |
| | | 100 | r | (247) | | | | | | | | | | |
| 1α,25-(OH)₂-22-ene-24,24-dihomo-D₃ | ZBV | 1 | r | (521) | 3 | (250) | | | 100.0 | h | (521) | 0 | sc | (521) |
| | | 3 | r | (250) | | | | | 10.00 | h | (250) | <0.001 | c | (250) |
| 22-dehydro-24,24,24-trihomo-1α,25-(OH)₂-D₃ | ZBW | 0.8 | r | (521) | 0.8 | (250) | | | 1.00 | h | (521) | 0 | sc | (521) |
| | | | | (250) | | | | | 0.5 | h | (250) | 0 | c | (250) |
| 26-homo-22-dehydro-1α,25(R)₂(OH)₂-D₃ | ZBX | 100 | c | (509, 247) | 100 | (249) | | | 10.00 | h | (249, 247) | 1 | sc | (509) |
| | | 100 | r | (249) | | | | | 1.40 | h | (201) | 1,>1 | c | (249) |
| 1α,(OH)₂-22-ene-24-oxo-26,27-dehydro-D₃ | ZDY | 0.3 | c | (522) | | | | | 0.01 | u | (522) | | | |
| (24S,25S)-25,26-epoxy-22-ene-1α,24-(OH)₂-D₃ | ZDZ | 8 | p | (204) | | | 3 | (204) | 0.15 | h | (204) | 0.01 | c | (204) |
| (24S,25R)-25,26-epoxy-22-ene-1α,24-(OH)₂-D₃ | ZCA | 8 | p | (204) | | | 2 | (204) | 0.30 | h | (204) | 0.01 | sc | (203) |
| (22E,24R)-1α,24-(OH)₂-22-dehydro-D₃ | ZCB | 10 | c | (203) | | | | | | | | 0.39 | sc | (203) |
| (22E,24S)-1α,24-(OH)₂-22-dehydro-D₃ | ZCC | 100 | c | (203) | | | | | | | | 0.95 | sc | (203) |
| (21S)-1α,25-(OH)₂-22-yne-D₃ | ZCD | 2 | r | (204) | | | 5 | (204) | 0.03 | h | (204) | <0.01 | c | (204) |
| 22,24-dinor-1,25-(OH)₂-D₃ | ZCE | | | | | | | | 0.004 | u | (192) | | | |
| 23-oxa-24,24b-dihomo-1α,25-(OH)₂-D₃ | ZCF | <100 | c | (348) | | | | | <1.00 | u | (348) | | | |
| 23-thia-1α,25-(OH)₂-D₃ | ZCG | | | | | | | | 0.20 | h | (212) | | | |
| 23-aza-1α,25-(OH)₂-D₃ | ZCH | | | | | | | | 0.13 | h | (242) | | | |
| 24,25-epoxy-26,27-dinor-23,23-dimethyl-1α-(OH)-D₃ | ZCI | 1 | p | (204) | | | 0 | (204) | 0.00 | h | (204) | <0.001 | c | (204) |
| 23-keto-25-(OH)-D₃ | ZCJ | | | | | | 11600 | (508) | | | | | | |
| 1α,25-(OH)₂-25,26-dehydro-D₃ | ZCK | 2 | b | (508) | | | | | 10.00 | h | (229) | 20.0 | c | (508) |
| 23(S)-OH-26,27-F₆-1α,25-(OH)₂-D₃ | ZCL | 30 | c | (230) | | | | | 0.004 | h | (193) | 1 | c | (210) |
| 24,15,26,27-tetranor-1,23-(OH)₂-D₃ | ZCM | | | | | | | | | | | | | |
| 23(S),25(R)-1α,25-(OH)₂-D₃-26,23-lactol | ZCN | | | | | | | | | | | <0.1 | sc | (195) |
| 1α,25-(OH)₂-16,21(Z)-diene-D₃ | ZCP | 145 | r | (187) | | | | | 1.00 | h | (187) | | | |
| 25,26-epoxy-22-yne-1α,(OH)-D₃ | ZCQ | 30 | p | (204) | | | 6 | (204) | 2.40 | h | (204) | 0.01 | c | (204) |
| 25-(OH)₂-24,26,23-trihomo-D₃ | ZCS | 18 | c | (244) | | | | | 5.00 | h | (244) | 0.2 | r | (244) |
| 1α,25-(OH)₂-24,26,23-trihomo-D₃ | ZCT | 10 | c | (244) | | | | | 20.00 | u | (244) | 30 | r | (244) |
| 22,23-difluoro-24-homo-1α,25-(OH)₂-D₃ | ZCU | 28 | c | (218) | | | | | 10.00 | h | (217) | 1,<1 | ci | (218) |
| 24R-(OH)-25-F-D₃ | ZCV | 0.3 | c | (213,560) | | | 0.15 | (218) | | | | >0.002 | r | (213) |
| 26,27-F₆-1α,24-(OH)₂-D₃ | ZCW | 60 | c | (223) | 60 | (223) | | | 10.00 | h | (223) | | | |

APPENDIX I (Continued)

| 1α,25-(OH)₂-VITAMIN D₃ ANALOG NAME | ANA-LOG CODE NAME | VIT D RECEPTOR (non Human) RCI | SPC | (ref) | VIT D RECEPTOR (HL-60) RCI | (ref) | D-BINDING PROTEIN RCI | (ref) | CELL DIFFERENTIATION ED50 | (s) | (ref) | CALCEMIC INDEX CI | (s) | (ref) |
|---|---|---|---|---|---|---|---|---|---|---|---|---|---|---|
| (24S,25S)-25,26-epoxy-1α,24-(OH)₂-D₃ | ZCX | 5 | p | (204) | | | 3 | (204) | 0.07 | h | (204) | 0.02 | c | (204) |
| (24R,25R)-25,26-epoxy-1α,24-(OH)₂-D₃ | ZCY | 20 | p | (204) | | | 73 | (204) | 0.12 | h | (204) | 0.01 | c | (204) |
| (24S,25R)-25,26-epoxy-1α,24-(OH)₂-D₃ | ZCZ | 10 | p | (204) | | | 7 | (204) | 0.44 | h | (204) | 0.03 | c | (204) |
| (24R,25S)-25,26-epoxy-1α,24-(OH)₂-D₃ | ZDA | 9 | p | (204) | | | 30 | (204) | 0.33 | h | (204) | 0.01 | c | (204) |
| (24R,25S)-25,26-epoxy-27-nor-1α,24-(OH)₂-D₃ | ZDB | 3 | p | (204) | | | 21 | (204) | <0.01 | h | (204) | <0.01 | c | (204) |
| (24S,25S)-25,26-epoxy-27-nor-1α,24-(OH)₂-D₃ | ZDC | 2 | p | (204) | | | 5 | (204) | <0.01 | h | (204) | <0.01 | c | (204) |
| 24,25-epoxy-1α,(OH)₂-D₃ | ZDD | 3 | p | (204) | | | 27 | (204) | 0.06 | h | (204) | 0 | c | (204) |
| 24-ene-D₃ | ZDE | | | | | | | | | | | 0 | sc | (549) |
| 1α-(OH)-24-ene-D₃ | ZDF | 0.2 | c | (190) | | | | | | | | 1,<1 | c,i | (218) |
| 24,24-difluoro-1α,25(OH)₂-26,27-dimethyl-D₃ | ZDH | 50 | c | (218) | | | 4 | (218) | | | | 0.50 | sc,c | (246) |
| 22,23-dihydro-24-epi-1α,25-(OH)₂-D₃ | ZDK | | | | | | | | 1.00 | h | (248) | | | |
| 25,26,27-trinor-1α,25-(OH)₂-D₃ | ZDL | | | | | | | | 0.01 | | (193) | | | |
| 25-aza-D₃ | ZDM | | | | | | | | | | | | | |
| 25,26-epoxy-1α,(OH)₂-D₃ | ZDN | 27 | p | (204) | | | 76 | (204) | 37.00 | h | (204) | 0.14 | c | (204) |
| 1α-(OH)-25-hydroxymethyl-D₃ | ZDO | | | | | | | | 0.14 | | (193) | | | |
| 1α-(OH)-25-F-D₃ | ZDP | 0.3 | c | (507) | | | | | | | | 0.0 | c | (186) |
| | | | | | | | | | | | | 0.02 | c,i | (507) |
| 1α,25-F₂-D₃ | ZDQ | | | | | | | | | | | 0 | sc | (490) |
| ZDR | ZDR | 100 | r | (249) | 100 | (249) | | | 10.00 | h | (249) | 1,>1 | c,i | (249) |
| 1α,25-(OH)₂-26-homo-D₃ | | 100 | c | (247) | | | | | 10.00 | h | (247) | | | |
| 1α,25-(OH)₂-26-homo-D₃ | | | | | | | | | 7.60 | h | (193) | | | |
| 26,27-dimethyl-1α,25-(OH)₂-D₃ | ZDV | 50 | c | (315,562) | 120 | (252,253) | 5 | (315, 562) | 2.50 | h | (217) | >1 | sc | (488) |
| | | 100 | c | (254) | | | | | 1.00 | | (252,253) | 0.5 | cbp | (515) |
| | | 110 | c | (568) | | | 10 | (252) | | | | | | |
| | | | | | | | | <100 | (254) | 2.50 | | (247) | >1,1 | i,c | (254) |
| | | | | | | | | | | | | >1 | c,i | (562) |
| | | | | | | | | | | | | <1 | sc | (247) |
| 26,27-diethyl-1α,25-(OH)₂-D₃ | ZDW | 16 | c | (254) | 20 | (252,253) | <1 | (252) | 10.00 | h | (217) | <1 | c,i | (254) |
| | | 25 | c | (568) | | | <10 | (254) | 0.20 | h | (252) | | | |
| | | | | | | | | | | 0.5 | | (253) | 0 | | (247) |
| | | | | | | | | | | 10.00 | h | (247) | | | |

APPENDIX I (Continued)

| 1α,25-(OH)₂-VITAMIN D₃ ANALOG NAME | ANALOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| 26,27-dipropyl-1α,25-(OH)₂-D₃ | ZDX | 3 | c | (354) | 3 (252,253) | | <1 | (252) | 0.10 | h | (252,253) | <1.0 | sc | (354) |
| | | 5 | c | (568) | | | <10 | (255) | | | | | | |
| 1α,23(S),25(R),26-(OH)₄D₃ | ZDY | | | | | | | | | | | | | |
| 1α-(OH)-26,27-F₆-D₃ | ZDZ | 1 | c | (223) | 1 (223) | | | | 1.00 | h | (223) | 0.05 sc | | (195) |
| 25-(OH)-26,27-F₆-D₃ | ZEA | | | | | | | | 0.08 | h | (1021) | | | |
| 26,27-dinor-1α,25-(OH)₂-D₃ | ZEB | | | | | | | | 0.01 | h | (217,193) | | | |
| 1α-(OH)-24-oxa-26,27-dehydro-D₁ | ZEC | | | | | | | | | | | | | |
| 23-oxa-26,27-dimethyl-1α,25-(OH)₂-D₁ | ZED | 50 | | (574) | | | <2 | (574) | 1 | h | (574) | <0.2 | u | (574) |
| 20-epi-23-oxa-26,27-dimethyl-1α,25-(OH)₂-D₁ | ZEE | 30 | p | (574) | | | <2 | (574) | 0.3 | h | (574) | 0.2 | u | (574) |
| 20,21-methano-23-oxa-26,27-dimethyl-1α,25-(OH)₂-D₁ | ZEF | 0 | p | (574) | | | <2 | (574) | 0.2 | h | (574) | 1 | u | (574) |
| 20-methyl-1,23-oxa-26,27-dimethyl-1α,25-(OH)₂-D₁ | ZEG | 50 | p | (574) | | | <2 | (574) | 0.5 | h | (574) | 0.2 | u | (574) |
| 22-ene-26-methyl-1α,25S(OH)₂D₁ | ZEH | 150 | c | (575) | | | | | 2.1 | h | (576) | 2.12/0.6 | c | (577) |
| 22-ene-26,27-dimethyl-1α,25-(OH)₂D₁ | ZEI | 80 | h | (578) | | | 0.75-r (205) <1 (578) | | 60 | h | (578) | | | |
| 22-ene-24-homo-26,27-dimethyl-1α,25-(OH)₂D₁ | ZEJ | | | | | | | | 20 | u | (485) | 0.2 | u | (485) |
| 20-epi-22-ene-24-homo-26,27-dimethyl-1α,25-(OH)₂D₁ | ZEK | | | | | | | | 1000 | u | (485) | 1.2 | u | (485) |
| 22-ene-26,27-dimethyl-1α,25-(OH)₂D₁ | ZEL | 90 | c | (486) | | | | | 1.5 | u | (486) | | | |
| 22-homo-26,27-dimethyl-1α,25-(OH)₂D₁ | ZEM | | | | | | | | 1.8 | u | (446) | | | |
| 22-ene-24-dihomo-26,27-dimethyl-1α,25-(OH)₂D₁ | ZEN | 2 | c | (486) | | | | | 0.1 | u | (486) | | | |
| 20-epi-22-ene-26,27-dimethyl-1α,25-(OH)₂D₁ | ZEO | 30 | c | (486) | | | | | 4 | u | (486) | | | |
| 20-epi-22-ene-24-homo-26,27-dimethyl-1α,25-(OH)₂D₁ | ZEP | 40 | c | (486) | | | | | 280 | u | (486) | | | |
| 20-epi-22-ene-24-dihomo-26,27-dimethyl-1α,25-(OH)₂D₁ | ZEQ | 7 | c | (486) | | | | | 490 | u | (486) | 0.6 | u | (486) |
| 20-epi-22-ene-24-trihomo-26,27-dimethyl-1α,25-(OH)₂D₁ | ZER | 80 | c | (486) | | | | | 25 | u | (486) | | | |
| 17(20)E-ene-22-yne-24-homo-26,27-dimethyl-1α,25-(OH)₂D₁ | ZES | 0.1 | c | (486) | | | | | 2.5 | u | (486) | | | |
| 17(20)Z-ene-22-yne-24-homo-26,27-dimethyl-1α,25-(OH)₂D₁ | ZET | 7 | c | (486) | | | | | 32 | u | (486) | 0.7 | u | (486) |
| 17(20)Z-ene-22-yne-24-dihomo-26,27-dimethyl-1α,25-(OH)₂D₁ | ZEU | 20 | c | (486) | | | | | 710 | u | (486) | | | |
| 17(20)Z-ene-22-yne-24-dihomo-26,27-dimethyl-1α,25-(OH)₂D₁ | ZEV | 2 | c | (486) | | | | | 290 | u | (486) | 0.25 | u | (486) |

APPENDIX I (Continued)

| 1α,25-(OH)₂ VITAMIN D₃ ANALOG NAME | ANA-LOG CODE NAME | VIT D RECEPTOR (non Human) | | | VIT D RECEPTOR (HL-60) | | D-BINDING PROTEIN | | CELL DIFFERENTIATION | | | CALCEMIC INDEX | | |
|---|---|---|---|---|---|---|---|---|---|---|---|---|---|---|
| | | RCI | SPC | (ref) | RCI | (ref) | RCI | (ref) | ED50 | (s) | (ref) | CI | (s) | (ref) |
| 20-ene-22-yne-26,27-dimethyl-1α,25-(OH)₂D₃ | ZEW | 90 | c | (486) | | | | | 1.4 | u | (486) | | | |
| 20-ene-22-yne-24-homo-26,27-dimethyl-1α,25-(OH)₂D₃ | ZEX | 3 | c | (486) | | | | | 1.2 | u | (486) | | | |
| 26,27-dimethyl-1α,20,25-(OH)₃D₃ | ZEY | 20 | ? | (542) | | | | | 100 | u | (542) | 0.06 | u | (542) |
| 24-homo-26,27-dimethyl-1α,20,25-(OH)₃D₃ | ZEZ | 0.6 | ? | (542) | | | | | 9 | u | (542) | <0.005 | u | (542) |
| 24-homo-26,27-dimethyl-1α,20,25-(OH)₃D₃ | ZFA | 50 | ? | (542) | | | | | 8000 | u | (542) | 0.3 | u | (542) |
| 20-methoxy-26,27-dimethyl-1α,25-(OH)₂D₃ | ZFB | 1 | ? | (542) | | | | | 100 | u | (542) | 0.06 | u | (542) |
| 20-methoxy-24-homo-26,27-dimethyl-1α,25-(OH)₂D₃ | ZFC | 7 | ? | (542) | | | | | 5000 | u | (542) | 0.1 | u | (542) |
| 20-ethoxy-26,27-dimethyl-1α,25-(OH)₂D₃ | ZFD | 1 | ? | (542) | | | | | 100 | u | (542) | | | |
| 20-ethoxy-24-homo-26,27-dimethyl-1α,25-(OH)₂D₃ | ZFE | 6 | c | (532) | | | | | 100 | u | (486) | 7.1 | u | (532) |
| 26,27-dimethyl-1α,22S,25-(OH)₃D₃ | ZFF | 2 | c | (532) | | | | | 20 | u | (532) | 0.8 | u | (532) |
| 24-homo-26,27-dimethyl-1α,22S,25-(OH)₃D₃ | ZFG | <0.5 | c | (532) | | | | | 100 | u | (532) | | | |
| 24-dihomo-26,27-dimethyl-1α,22S,25-(OH)₃D₃ | ZFH | 0.5 | c | (532) | | | | | 100 | u | (532) | | | |
| 21-yne-24-dihomo-26,27-dimethyl-1α,22S,25-(OH)₃D₃ | ZFI | <0.3 | c | (532) | | | | | 1 | u | (532) | | | |
| 21-yne-24-trihomo-26,27-dimethyl-1α,22S,25-(OH)₃D₃ | ZFJ | <3 | c | (532) | | | | | 1 | u | (532) | | | |
| 23-yne-26,27-dimethyl-1α,22S,25-(OH)₃D₃ | ZFK | 0.5 | c | (532) | | | | | 0.1 | u | (532) | | | |
| 23-yne-24-homo-26,27-dimethyl-1α,22S,25-(OH)₃D₃ | ZFL | <0.5 | c | (532) | | | | | 0.5 | u | (532) | | | |
| 23-yne-24-dihomo-26,27-dimethyl-1α,22S,25-(OH)₃D₃ | ZFM | <0.3 | c | (532) | | | | | <0.01 | u | (532) | | | |
| 23-yne-24-trihomo-26,27-dimethyl-1α,22S,25-(OH)₃D₃ | ZFN | 40 | c | (532) | | | | | 1000 | u | (532) | 12 | u | (532) |
| 22R-methoxy-23-yne-24-homo-26,27-dimethyl-1α,25-(OH)₂D₃ | ZFO | 10 | c | (532) | | | 110 | (532) | 200 | u | (532) | | | |
| 23-oxa-26,27-diethyl-1α,25-(OH)₂D₃ | ZFP | 10 | p | (574) | | | <2 | (574) | 0.25 | h | (574) | 0.01 | u | (574) |
| 20-ene-23-oxa-26,27-diethyl-1α,25-(OH)₂D₃ | ZFQ | 25 | p | (574) | | | <2 | (574) | 0.2 | h | (574) | 0.01 | u | (574) |
| 20,21-methano-23-oxa-26,27-diethyl-1α,25-(OH)₂D₃ | ZFR | 50 | p | (574) | | | <2 | (574) | 0.1 | h | (574) | 0.001 | u | (574) |
| 20-epi-22-oxa-24-dihomo-26,27-dimethyl-1α,25-(OH)₂D₃ | ZFS | 60 | c | (525) | | | | | 400 | u | (525) | 0.8 | u | (525) |
| 26,27-diethyl-1α,20,25-(OH)₃D₃ | ZFT | 0.5 | ? | (542) | | | | | <0.1 | u | (542) | | | |
| 20-methoxy-26,27-diethyl-1α,25-(OH)₂D₃ | ZFU | 0.9 | ? | (542) | | | | | 0.1 | u | (542) | | | |
| 22-ene-26,27-dehydro-1α,21R-(OH)₂D₃ | ZFV | | | | | | | | 0.01 | u | (485) | <0.01 | u | (485) |
| 20-epi-22-ene-26,27-dehydro-1α,24S-(OH)₂D₃ | ZFW | | | | | | | | 0.1 | u | (485) | <0.01 | u | (485) |
| 20-epi-22-ene-26,27-dehydro-1α,24R-(OH)₂D₃ | ZFX | | | | | | | | 1 | u | (485) | <0.01 | u | (485) |
| 24-dihomo-26,27-diethyl-1α,25-(OH)₂D₃ | ZFY | | | | | | | | 0.01 | u | (489) | | | |
| 20-epi-24-homo-26,27-diethyl-1α,25-(OH)₂D₃ | ZFZ | | | | | | | | 100 | u | (495) | <0.26 | u/sc | (495) |
| 22-oxa-26,27-diethyl-1α,25-(OH)₂D₃ | ZGA | | | | | | | | 1 | h | (139) | | | |

We claim:

1. A method for the treatment of a hyperproliferative disease in a subject, wherein the hyperproliferative disease responds to treatment with a Vitamin D drug, comprising repeatedly administering to the subject a therapeutically effective pulse dose of the Vitamin D drug, no more frequently than once in three days, in a pulse dose of about 0.12 mcg/kg per day to about 2.8 mcg/kg per day, each pulsed dose being in a sufficient amount to have an antiproliferative effect, without inducing severe symptomatic hypercalcemia in the subject, wherein the Vitamin D drug is 25-hydroxyvit $D_3$ or 1,25-dihydroxycholecalciferol.

2. The method of claim 1, comprising administering the Vitamin D drug to a subject having a neoplasm that expresses a Vitamin D receptor, wherein the therapeutically effective pulse dose is an anti-neoplastic dose.

3. The method of claim 2, wherein the neoplasm is selected from the group of cancer of the prostate, breast, colon, lung, head ad neck, pancreas, endometrium, bladder, cervix, ovaries, squamous cell carcinoma, renal cell carcinoma, myeloid and lymphocytic leukemia, lymphoma, medullary thyroid carcinoma, melanoma, multiple myeloma, retinoblastoma, and sarcomas of the soft tissues and bone.

4. The method of claim 3, wherein the neoplasm is breast cancer or prostate cancer.

5. The method of claim 1, wherein each dose of the Vitamin D drug is administered in an amount that raises a serum level of the Vitamnin D drug in the subject with a tumor to a supraphysiologic amount for a sufficient period of time to induce differentiation or regression of the tumor without causing symptomatic hypercalcemia.

6. The method of claim 1, wherein the Vitamin D drug is calcitriol, which is administered in a therapeutically effective pulse dose no more than once in five days.

7. The method of claim 6, wherein the calcitriol is administered orally in a dose of at least 0.12 mcg/kg per day no more than once in five days.

8. The method of claim 6, wherein the calcitriol is administered orally in a dose of at least 0.48 mcg/kg or about 1 mcg/kg per day no more than once in a week.

9. A method of treating a tumor in a subject, wherein the tumor expresses a Vitamin D receptor and is responsive to treatment with a Vitamin D drug, the method comprising repeatedly administering orally to the subject, once in a three to ten day period, a dose of calcitriol, wherein each dose of calcitriol is a therapeutically effective dose, of about 0.12 mcg/kg to about 2.8 mcg/kg, sufficient to have an antiproliferative effect, without inducing severe symptomatic hypercalcemia in the subject.

10. The method of claim 9, wherein the calcitriol is administered to the subject no more than once per week.

11. The method of claim 1, wherein the subject eats a reduced calcium diet for a sufficient period of time prior to administration of the Vitamin D drug to reduce absorption of dietary calcium.

12. A method of treating in a subject a tumor that expresses a Vitamin D receptor, the method comprising repeatedly administering a dose of a Vitamin D drug to raise a blood level of the Vitamin D drug to a sufficiently supraphysiologic level for a sufficient period of time to inhibit growth of the tumor, wherein each dose of the Vitamin D drug is sufficient to inhibit tumor growth without inducing hypercalcemia in the subject, wherein the Vitamnin D drug is 25-hydroxyvitamin $D_3$ or 1,25-dihydroxycholecalciferol and the dose is administered no more than once in 3–10 days, and wherein the Vitamin D drug is admistered in a dose of about 0.12 mcg/kg per day to about 2.8 mcg/kg per day.

13. The method of claim 12, wherein the Vitamin D drug comprises calcitriol.

14. The method of claim 13, wherein the calcitriol is administered in a dose of about 0.50 mcg/kg per day once per week.

15. A method of administering a Vitamin D drug to a subject in need thereof, the method comprising repeatedly administering therapeutically effective pulse doses of the Vitamin D drug wherein each dose is sufficient to achieve intermittent antiproliferative therapeutic levels of the Vitamin D drug, and wherein the pulse doses are administered separated by 3–10 days to avoid symptomatic hypercalcemia, and wherein each dose is about 0.12 mcg/kg per day to about 2.8 mcg/kg per day and the Vitamin D drug is 25-hydroxyvitamin $D_3$ or 1,25-dihydroxycholecalciferol.

16. The method of claim 15, wherein the method comprises treating a hyperproliferative disorder in the subject.

17. The method according to claim 16 wherein the hyperproliferative disorder is a hyperproliferative skin disease.

18. The method according to claim 17 wherein the hyperproliferative skin disease is selected from the group consisting of psoriasis, disorders of keratinization, keratosis, disorders of sebaceous glands, and combinations thereof.

19. The method according to claim 18 wherein the hyperproliferative skin disease comprises disorders of sebaceous glands.

20. The method of claim 19, wherein the hyperproliferative skin disease comprises acne or sebonheic dermatitis.

21. The method according to claim 1 wherein the hyperproliferative disorder comprises a hyperproliferative skin disease.

22. The method according to claim 21 wherein the hyperproliferative skin disease is selected from the group consisting of psoriasis, disorders of keratinization, keratosis, disorders of sebaceous glands, and combinations thereof.

23. The method according to claim 22 wherein the hyperproliferative skin disease comprises disorders of sebaceous glands.

24. The method of claim 19, wherein the hyperproliferative skin disease comprises acne or seborrheic dermatitis.

25. The method of claim 15, wherein each dose of the Vitamin D drug achieves a serum level of about 0.5–25 nM of the drug.

26. The method of claim 25, wherein each dose of the Vitamin D drug achieves a serum level of about 1–25 nM of the drug.

27. The method of claim 25, wherein each dose of the Vitamin D drug achieves a serum level of about 5–10 nM of the drug.

28. The method of claim 15, wherein the drug is administered in a dose of at least 0.12 mcg/kg per day no more than once every 5 or 6 days.

29. The method of claim 28, wherein the drug is administered no more than once a week.

30. The method of claim 29, wherein the drug is administered in a dose of at least 0.48 mcg/kg per day no more than once per week.

31. The method of claim 30, wherein the drug is administered in a dose of about 2.80 mcg/kg per day.

32. The method of claim 29, wherein the drug is administered in a dose of about 0.24 to about 2.80 mcg/kg per day.

33. The method of claim 15, wherein the drug is administered orally, intravenously, parenterally, rectally, topically, nasally or transdermally.

34. The method of claim 33, wherein the drug is admitered orally.

35. The method of claim 15, wherein the drug is administered in conjunction with an other therapeutic agent.

36. The method of claim 35, wherein the other therapeutic agent is an osteoclast inhibitor.

37. The method of claim 36, wherein the osteoclast inhibitor comprises a biphosphonate osteoclast inhibitor.

38. The method of claim 15, wherein the method further comprises administering to the subject an initial dose of the drug, followed by a series of pulsed administrations of an escalated dose, wherein each pulsed administration is in an amount sufficient to have an antiproliferative effect, and wherein each subsequent administration follows the preceding administration by a period of time sufficient to avoid symptomatic hypercalcemia in the subject.

39. The method of claim 15, wherein serum levels of calcium return to normal levels of calcemia between doses of the drug.

40. The method of claim 15, wherein the drug would induce hypercalcemia if administered daily at the dose at which it is administered in pulse doses separated by 3–10 days.

41. A method of administering a Vitamin D drug to a subject at an anti-hyperproliferative dose substantially without symptomatic significant hypercalcemia, wherein the method comprises repeatedly administering therapeutically effective pulsed doses of the Vitamin D drug, wherein each dose of the Vitamin D drug is a dose that is sufficient to have an antiproliferative effect, the dose is repetitively administered separated by 3–10 days, and the Vitamin D drug is calcitriol, and wherein the dose is about 0.12 mcg/kg per day to about 2.8 mcg/kg per day.

42. The method of claim 41, wherein each dose of the drug is sufficient to have an anti-tumor antiproliferative effect.

43. The method of claim 42, wherein the dose of the drug is sufficient to raise a serum level of the drug to 0.5–25 nM.

44. The method of claim 42, wherein the dose of the drug is about 0.48–2.80 mcg/kg.

45. The method of claim 42, comprising administering the Vitamin D drug to a subject having a neoplasm that expresses a Vitamin D receptor.

46. The method of claim 42, wherein the neoplasm is selected from the group of cancer of the prostate, breast, colon, lung, head and neck, pancreas, endometrium, bladder, cervix, ovaries, squamous cell carcinoma, renal cell carcinoma, myeloid and lymphocytic leukemia, lymphoma, medullary thryoid carcinoma, melanoma, multiple myeloma, retinoblastoma, and sarcomas of the soft tissues and bone.

47. The method of claim 44, wherein the dose is administered orally.

48. The method of claim 41, wherein the doses are separated by 7–10 days.

49. The method of claim 43, wherein the dose of the drug is sufficient to raise the serum level of the drug to 0.5–25 nM for no more than about 6 hours.

50. The method of claim 15, wherein the pulse dose is administered in divided doses over a one day period.

51. The method of claim 41, wherein each pulse dose is administered in divided doses over a one day period.

52. The method of claim 15, wherein each pulse dose is administered as a single dose.

53. The method of claim 41, wherein each pulse dose is administered as a single dose.

54. The method of claim 1, wherein the Vitamin D drug is calcitriol, which is administered in a dosage form that contains 5–100 mcg calcitriol.

* * * * *